United States Patent
Uematsu et al.

(10) Patent No.: US 7,867,348 B2
(45) Date of Patent: Jan. 11, 2011

(54) NON-WOVEN FABRIC, NON-WOVEN FABRIC MANUFACTURING METHOD AND ABSORBENT ARTICLE

(75) Inventors: Katsuhiro Uematsu, Kagawa (JP); Hideyuki Ishikawa, Kagawa (JP); Koichiro Tani, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 414 days.

(21) Appl. No.: 11/950,899

(22) Filed: Dec. 5, 2007

(65) Prior Publication Data

US 2008/0132136 A1 Jun. 5, 2008

(30) Foreign Application Priority Data

Dec. 5, 2006 (JP) .............................. 2006-328674
Dec. 12, 2006 (JP) .............................. 2006-335153

(51) Int. Cl.
*D04H 1/50* (2006.01)
(52) U.S. Cl. ..................................... 156/84; 264/342 R
(58) Field of Classification Search .................. 156/85, 156/84; 264/342 R; 604/378–380; 428/218
See application file for complete search history.

(56) References Cited

U.S. PATENT DOCUMENTS

| | | | | |
|---|---|---|---|---|
| 3,615,978 A | * | 10/1971 | Lissalde ....................... | 156/84 |
| 3,889,325 A | * | 6/1975 | Fleissner ..................... | 26/18.5 |
| 4,027,672 A | * | 6/1977 | Karami ........................ | 604/380 |
| 4,999,232 A | | 3/1991 | LeVan | |
| 5,229,184 A | | 7/1993 | Campbell et al. | |
| 5,509,915 A | | 4/1996 | Hanson et al. | |
| 2004/0224136 A1 | | 11/2004 | Collier, IV et al. | |
| 2005/0042446 A1 | | 2/2005 | Kim et al. | |
| 2010/0137824 A1 | | 6/2010 | Uematsu et al. | |

FOREIGN PATENT DOCUMENTS

| | | |
|---|---|---|
| DE | 13 03 780 | 10/1972 |
| DE | 38 37 685 | 7/1989 |
| JP | 04221556 | 8/1992 |
| JP | 04272261 | 9/1992 |
| JP | 10137167 | 5/1998 |
| JP | 2000-262558 | 9/2000 |
| JP | 2001-328191 | 11/2001 |
| JP | 2002136547 | 5/2002 |
| JP | 2004-033236 | 2/2004 |

OTHER PUBLICATIONS

International Search Report mailed on Jun. 24, 2008, directed to International Patent Application No. PCT/JP2008/057238; 4 pages.
European Search Report dated Jul. 27, 2010, directed to counterpart European Application No. 07 85 9704; 3 pages.

* cited by examiner

*Primary Examiner*—Michael A Tolin
(74) *Attorney, Agent, or Firm*—Morrison & Foerster LLP

(57) ABSTRACT

The present invention aims at providing a non-woven fabric having high-density regions and low-density regions dispersed horizontally, so as not to prevent liquid transfer from a surface sheet to an absorbent body and not to diffuse a liquid less during transfer, a manufacturing method thereof, and a disposable diaper made therefrom. The non-woven fabric 5 includes a plurality of high-density regions 11 and a plurality of low-density regions 12 dispersedly formed in a planar direction thereof. The high-density regions 11 are formed dominantly on at least one side of the non-woven fabric 5, and the low-density regions 12 are formed communicating both sides thereof.

7 Claims, 13 Drawing Sheets

NON-WOVEN FABRIC, NON-WOVEN FABRIC MANUFACTURING METHOD AND ABSORBENT ARTICLE

This application is based on and claims the benefit of priority from Japanese Patent Application No. 2006-328674, filed on 5 Dec. 2006 and Japanese Patent Application No. 2006-335153, filed on 12 Dec. 2006, the content of which is incorporated herein by reference.

BACKGROUND OF THE INVENTION

1. Field of the Invention

The present invention relates to a non-woven fabric, a non-woven fabric manufacturing method and an absorbent article.

2. Related Art

Conventionally, various improvements have been made in a selection of fiber and a structure of a non-woven fabric for improvement of a liquid-drawing ability and a liquid-transfer property (spot property), for example. Here, a high liquid-drawing ability indicates not preventing a liquid transfer from a surface sheet to an absorbent body, and a high spot property indicates diffusing less liquid during transfer.

For example, Japanese Unexamined Patent Application, First Publication No. 2004-33236 (hereinafter referred to as "Patent Document 1") discloses an absorbent article with a liquid permeable sheet made from fiber arranged between a liquid permeable surface sheet and a liquid retentive absorbent body. The liquid permeable sheet has a multilayer structure composed of a first layer arranged close to the absorbent body and a second layer arranged close to the surface sheet having higher density than the first layer, thus a liquid is transferred by capillary action from the second layer to the first layer.

SUMMARY OF THE INVENTION

However, although the liquid permeable sheet of Patent Document 1 does not prevent liquid transfer from the surface sheet to the absorbent body, it does not substantially realize the high spot property in parallel. Moreover, an overall density of the first layer arranged closest to the absorbent body is high, and thus the surface sheet may not transfer a large amount of discharged liquid appropriately to the absorbent body.

The present invention has been made in view of the foregoing problem, and aims at providing a non-woven fabric having high-density regions and low-density regions dispersed in a planar direction, thereby not preventing liquid transfer from a surface sheet to an absorbent body and diffusion of a liquid less during transfer; a manufacturing method thereof; and a disposable diaper made therefrom.

The inventor has found that, by pressing in the thickness direction a plurality of convex portions generated by heat-processing a fiber web including a heat-adhesive heat-shrinkable fiber, high-density regions and low-density regions are dispersedly formed in a planar direction, thereby reaching completion of the present invention. Additionally, the present inventors have found that, by heating a fiber web including heat-adhesive fiber and heat-shrinkable fiber in a predetermined condition, high-density regions and low-density regions are dispersedly formed in a planar direction and a non-woven fabric can be produced diffusing a liquid less during transfer and not preventing liquid transfer from a surface sheet to an absorbent body, thereby reaching completion of the present invention.

According to a first aspect of the present invention, a substantially uniformly-thick non-woven fabric including heat-adhesive heat-shrinkable fiber is provided, including a plurality of high-density regions being formed dominantly in at least one side in a thickness direction of the non-woven fabric and having a higher density than an average density of the non-woven fabric and a plurality of low-density regions having a lower density than the average density, in which the plurality of high-density regions and the plurality of low-density regions are dispersedly formed in a planar direction vertical to a thickness direction and at least a portion of the plurality of low-density regions is formed communicating both sides in the thickness direction.

In a second aspect of the non-woven fabric as described in the first aspect of the present invention, an index of dispersion of the plurality of high-density regions and the plurality of low-density regions is in the range of 250 to 450.

According to a third aspect of the present invention, a non-woven fabric manufacturing method is provided for a substantially uniformly-thick non-woven fabric including heat-adhesive heat-shrinkable fiber, having a plurality of high-density regions being formed dominantly in at least one surface and having a higher density than an average density of the non-woven fabric and a plurality of low-density regions having a lower density than the average density, in which the plurality of high-density regions and the plurality of low-density regions are dispersedly formed in a planar direction vertical to a thickness direction of the non-woven fabric and at least a portion of the plurality of low-density regions is formed communicating both sides in the thickness direction, including: a heat shrinkage process in which a fiber web including the heat-adhesive heat-shrinkable fiber is heat-processed at a temperature at which the heat-shrinkable fiber can be melted and shrunk; and a pressing process in which a plurality of convex portions, generated on at least one side of the fiber web by a heat-process in the heat shrinkage process which heat-shrinks the heat-shrinkable fiber, is pressed in a thickness direction of the fiber web.

According to a fourth aspect of the non-woven fabric manufacturing method as described in the third aspect of the present invention, in the heat shrinkage process, the fiber web is heat-processed while being supported vertically from below by way of a lower supporting member having a substantially planate surface, with the heat-shrinkable fiber being restrained from heat-shrinking on a side supported by the lower supporting member; in the pressing process, the heat-processed fiber web is pressed from an opposite side of the side supported by the lower supporting member.

According to a fifth aspect of the present invention, a substantially uniformly-thick non-woven fabric including a heat-adhesive fiber and a heat-shrinkable fiber having crimpability at least when heat-shrunk is provided, including a plurality of high-density regions being formed mainly of the heat-shrinkable fiber being heat-shrunk and having a higher density than an average density of the non-woven fabric and a plurality of low-density regions formed mainly of the heat-adhesive fibers being adhered to each other having a lower density than the average density, in which the plurality of high-density regions and the plurality of low-density regions are dispersedly formed in a planar direction vertical to a thickness direction and at least a portion of the plurality of low-density regions is formed communicating both sides in the thickness direction.

In a sixth aspect of the non-woven fabric as described in the fifth aspect of the present invention, the heat-shrinkable fiber can be shrunk at a higher temperature than the temperature at which the heat-adhesive fiber can be melted.

In a seventh aspect of the non-woven fabric as described in the fifth or sixth aspect of the present invention, an index of dispersion of the plurality of high-density regions and the plurality of low-density regions is in a range of 250 to 790.

According to an eighth aspect of the present invention, a non-woven fabric manufacturing method is provided for a substantially uniformly-thick non-woven fabric including a heat-adhesive fiber and a heat-shrinkable fiber having crimpability at least when heat-shrunk, including a plurality of high-density regions being formed mainly of the heat-shrinkable fiber being heat-shrunk and having a higher density than an average density of the non-woven fabric and a plurality of low-density regions formed mainly of the heat-adhesive fibers being adhered to each other having a lower density than the average density, in which the plurality of high-density regions and the plurality of low-density regions are dispersedly formed in a planar direction vertical to a thickness direction and at least a portion of the plurality of low-density regions is formed communicating both sides in the thickness direction, including: a feeding process in which a fiber web including the heat-adhesive fiber and the heat-shrinkable fiber is conveyed to a predetermined heating device; and a heat shrinkage process in which the fiber web is conveyed to a predetermined direction and heat-processed at a temperature at which the heat-shrinkable fiber can be shrunk; in which a condition of the high- and low-density regions is regulated by adjusting a feeding speed of the fiber web in at least one of the feeding process and the heat shrinkage process.

In a ninth aspect of the non-woven fabric manufacturing method as described in the eighth aspect of the present invention, the feeding speed of the fiber web in the heat-shrinkage process is adjusted so that a ratio of the feeding speed of the fiber web in the heat shrinkage process to the feeding speed of the fiber web in the feeding process is larger than a heat-shrinkage ratio of the fiber web at the temperature in the heat shrinkage process.

In a tenth aspect of the non-woven fabric manufacturing method as described in the eighth or ninth aspect of the present invention, a pre-heating process is included prior to the heat-shrinkage process, in which the fiber web is heated at the temperature at which the heat-adhesive fiber is not substantially melted and the heat-shrinkable fiber is not substantially shrunk, to limit a degree of freedom of the heat-shrinkable fiber by thinning a thickness of the fiber web.

In an eleventh aspect of the non-woven fabric manufacturing method as described in any one of the eighth to tenth aspects of the present invention, a heat-fusion process is included prior to the heat-shrinkage process, in which the fiber web is heated at the temperature at which the heat-adhesive fiber may be melted and the heat-shrinkable fiber is not substantially shrunk.

In a twelfth aspect of the non-woven fabric manufacturing method as described in any one of the eighth to eleventh aspects of the present invention, in the heat shrinkage process, the fiber web is conveyed while being arranged between an air permeable first supporting member and an air permeable second supporting member which is arranged vertically above and substantially parallel to the first supporting member with a predetermined distance away therefrom, and is heat-processed while being at least partially spaced apart from at least one of the first supporting member and the second supporting member by emitting heated air of a predetermined temperature from vertically under the first supporting member and emitting heated air of a predetermined temperature from vertically above the second supporting member.

According to a thirteenth aspect of the present invention, an absorbent article is provided including a surface sheet which is at least partially liquid permeable, a liquid-impermeable back sheet, an absorbent body disposed between the surface sheet and the back sheet, and a second sheet arranged between the surface sheet and the absorbent body, in which: the second sheet includes a substantially uniformly-thick non-woven fabric including heat-adhesive heat-shrinkable fiber; the non-woven fabric includes a plurality of high-density regions being formed dominantly in at least one side to a thickness direction of the non-woven fabric and having a higher density than an average density of the non-woven fabric and a plurality of low-density regions having a lower density than the average density; the plurality of high-density regions and the plurality of low-density regions are dispersedly formed in a planar direction vertical to a thickness direction; and at least a part of the plurality of low-density regions is formed communicating both sides in the thickness direction. According to a fourteenth aspect of the present invention, an absorbent article is provided including a surface sheet which is at least partially liquid permeable, a liquid-impermeable back sheet, an absorbent body disposed between the surface sheet and the back sheet, and a second sheet arranged between the surface sheet and the absorbent body, in which: the second sheet includes a substantially uniformly-thick non-woven fabric including a heat-adhesive fiber and a heat-shrinkable fiber having crimpability at least when heat-shrunk; the non-woven fabric includes a plurality of high-density regions being formed mainly of the heat-shrinkable fiber being heat-shrunk and having a higher density than an average density of the non-woven fabric and a plurality of low-density regions formed mainly of the heat-adhesive fibers being adhered to each other having a lower density than the average density; the plurality of high-density regions and the plurality of low-density regions are dispersedly formed in a planar direction vertical to a thickness direction; and at least a part of the plurality of low-density regions is formed communicating both sides in the thickness direction.

It should be noted that, with fibers of sheath-core structure used in the present invention, a ratio of a core to a sheath is in a mass ratio.

The present invention can provide a non-woven fabric having high-density regions and low-density regions dispersed in a planar direction, thereby not preventing liquid transfer from a surface sheet to an absorbent body and diffusing a liquid less during transfer, a manufacturing method thereof, and a disposable diaper made therefrom.

DETAILED DESCRIPTION OF THE INVENTION

Preferred embodiments of the present invention are explained with reference to the drawings.

Figure 1:
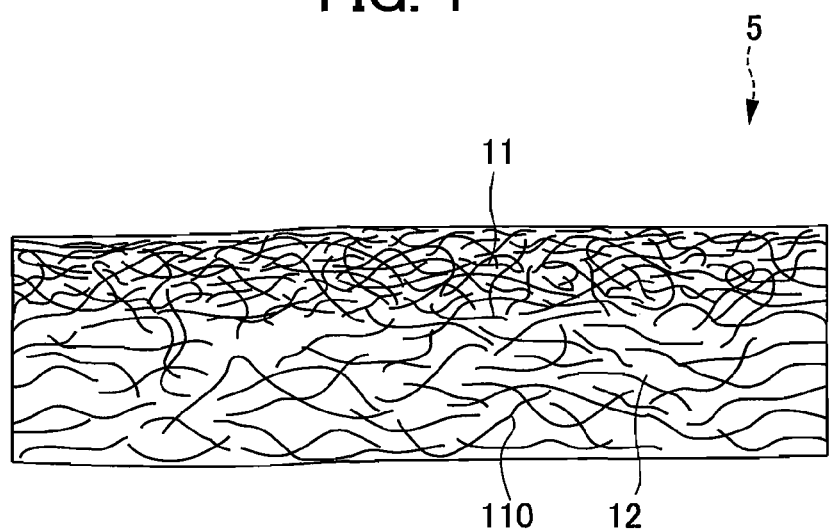
FIG. 1 is a cross-sectional view showing the non-woven fabric in the first embodiment of the present invention.
Figure 2:
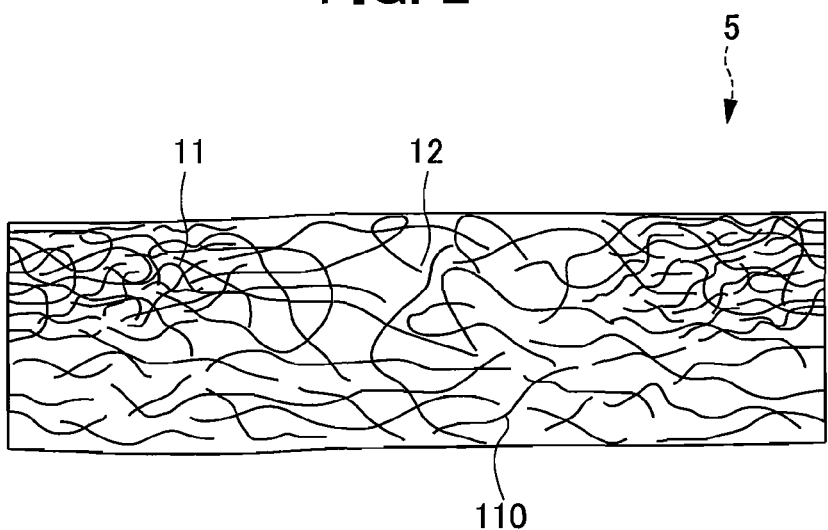
FIG. 2 is a partially enlarged view of FIG. 1.

A preferred embodiment of the present invention, the first embodiment, is described below with reference to FIGS. 1 and 2. A non-woven fabric 5 is a substantially uniformly-thick non-woven fabric including a heat-adhesive heat-shrinkable fiber 110 as shown in FIGS. 1 and 2, including a plurality of high-density regions 11 being formed dominantly in one side or both sides in a thickness direction of the non-woven fabric 5 and having a higher density than an average density of the non-woven fabric 5 and a plurality of low-density regions 12 having a lower density than the average density.

Figure 3:
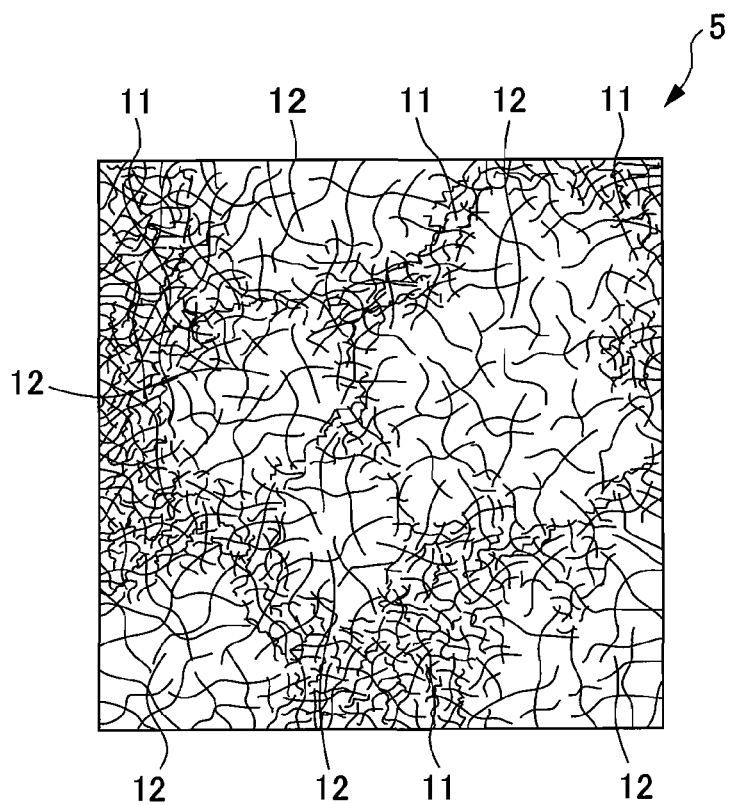
FIG. 3 is a top view of the non-woven fabric in the first embodiment.

The plurality of high-density regions 11 and the plurality of low-density regions 12 are dispersedly formed in a planar direction vertical to a thickness direction of the non-woven fabric 5 as shown in FIG. 3. At least a portion of the plurality of low-density regions 12 is formed communicating both sides in the thickness direction of the non-woven fabric 5 as shown in FIG. 2.

In the non-woven fabric 5 of the first embodiment, for example, a plurality of high-density regions 11 are formed dominantly on a predetermined side by pressing convex portions generated on the predetermined side by shrinkage of the heat-shrinkable fiber 110.

Examples of the heat-shrinkable fiber 110 include an eccentric sheath-core type composite fiber consisting of two thermoplastic polymer materials of different shrinkage ratios, and a side-by-side composite fiber. Examples of a pair of thermoplastic polymer materials of different shrinkage ratio include a combination of ethylene-propylene random copolymer and polypropylene, a combination of polyethylene and ethylene-propylene random copolymer, and a combination of polyethylene and polyethylene terephthalate. Specific examples are PEK and FCK manufactured by Toyobo Co., Ltd. and EP manufactured by Chisso Corporation.

A ratio of the heat-shrinkable fiber 110 in the non-woven fabric 5 is preferably 30 to 100% by mass, and more preferably 70 to 100% by mass. In a case in which the heat-shrinkable fiber 110 is included in the abovementioned ratio, the high-density regions 11 and the low-density regions 12 are dispersedly formed in a planar direction of the non-woven fabric 5.

The heat-shrinkable fiber 110 is, for example, a short staple fiber of which the length is preferably 5 to 90 mm and the thickness is preferably 1 to 11 dtex.

A heat shrinkage ratio of the heat-shrinkable fiber 110 at a predetermined temperature (for example, a heat-process temperature in a heat-fusion shrinkage process as described later) is 10 to 40%. The method for measuring the heat shrinkage ratio is as follows: (1) produce a 200 g/m² web using 100% of the fiber to be measured; (2) cut in a dimension of 250 mm×250 mm; (3) leave the sample in an oven at a predetermined temperature for 5 minutes; (4) measure the length after shrinkage; and (5) calculate the heat shrinkage ratio from the difference in lengths before and after heat shrinkage.

In a case in which the heat-shrinkable fiber 110 has the abovementioned heat-shrinkage ratio, the high-density regions 11 and the low-density regions 12 are appropriately formed. For example, by heating a fiber web containing a heat-shrinkable fiber 110 having the abovementioned heat shrinkage ratio, with one surface being supported by a supporting member, a non-woven fabric (fiber web) can be obtained with concave portions and convex portions (sea-island structure) formed on a free surface not supported by the supporting member. Then, by pressing the convex portions formed on the free surface in a thickness direction, the non-woven fabric 5 of the first embodiment can be obtained.

A temperature at which the heat-shrinkable fiber 110 is heat shrunk is higher than a temperature at which the heat-shrinkable fiber 110 is melted. In other words, if the heat-shrinkable fiber 110 is heat-processed at the shrinking temperature, the heat-shrinkable fiber 110 is melted at the same time and is bound to a fiber in contact therewith.

The high-density regions 11 are formed dominantly on one or both sides in a thickness direction of the non-woven fabric 5. The high-density regions 11 are formed, for example, in a predetermined area including a surface on one or both sides in a thickness direction of the non-woven fabric 5. The high-density regions 11 are formed mainly of the heat-shrinkable fiber 110 being heat-shrunk and having a higher density than an average density of the non-woven fabric 5.

The high-density regions 11 are formed by pressing, in a thickness direction of the non-woven fabric 5, a concavo-convex structure (sea-island structure) generated on a predetermined surface of the non-woven fabric 5 by heat-shrinkage of the heat-shrinkable fiber 110. In other words, by pressing the convex portions of the concavo-convex structure so that the convex portions have substantially the same thickness as concave portions, a density in the concave portions can be elevated. The convex portions being pressed become the high-density regions 11.

The low-density regions 12 are, as shown in FIGS. 1 and 2, formed mainly of the heat-shrinkable fiber 110 being adhered to each other and having a lower density than an average density of the non-woven fabric 5. The low-density regions 12 correspond to the concave portion (sea portion) in the concavo-convex structure (sea-island structure). The low-density regions 12 are formed communicating both sides in the thickness direction of the non-woven fabric 5 as shown in FIG. 2. The low-density regions 12 formed communicating both sides in the thickness direction of the non-woven fabric 5 allow for appropriate transfer of a liquid on one side of the non-woven fabric 5 to the other side.

The concavo-convex structure, for forming the high-density regions 11 and the low-density regions on the non-woven fabric 5, is provided by bringing (for example, collecting), in a stretching direction of the heat-shrinking fiber 110, a fiber tangled in or arranged in proximity of the heat-shrinking fiber 110 as the heat-shrinking fiber 110 is heat-shrunk. In other words, a region in which the heat-shrinking fiber 110 is heat-shrunk becomes a convex portion (island portion) and a sparse fiber region due to the removal of fibers by the heat-shrinking fiber 110 becomes a concave portion (sea portion). The convex portions and the concave portions of the concavo-convex structure (sea-island structure) are dispersedly formed in a planar direction of the non-woven fabric 5 (fiber web).

In addition, the low-density regions 12 are dispersedly formed in a planar direction of the non-woven fabric 5 and around each of the high-density regions 11, as shown in FIG. 3. Since the low-density regions 12 are formed around the high-density regions 11, a liquid drawn by the high-density regions 11 is led to the low-density regions 12 and appropriately transferred by the low-density regions 12 in a predetermined direction in a thickness direction of the non-woven fabric 5.

The distance between fibers in the high-density regions 11 is preferably 15 to 95 µm. The distance between fibers in the low-density regions 12 is preferably 85 to 390 µm.

The high-density regions 11 and the low-density regions 12 are dispersedly formed in a planar direction of the non-woven fabric 5. The degree of dispersion in the planar direction can be represented by, for example, the index of dispersion (standard deviation of average absorbance). An index of dispersion for the non-woven fabric 5 of the first embodiment is preferably 250 to 459, and more preferably 280 to 410.

When the index of dispersion is smaller than 250, the concavo-convex structure becomes nearly even. Consequently, a property of the low-density regions 12 diffusing a liquid less during transfer and a property of the high-density regions 11 not preventing liquid transfer in a thickness direction of the non-woven fabric may not be provided at the same time. When the index of dispersion is larger than 450, the concavo-convex structure becomes too uneven and a liquid temporarily captured in the low-density regions 12 cannot be transferred to the high-density regions 12. Consequently, a property of the low-density regions 12 diffusing a liquid less during transfer and a property of the high-density regions 11 not preventing a liquid transfer in a thickness direction of the non-woven fabric may not be provided at the same time.

The index of dispersion (standard deviation of average absorbance) can be measured and calculated by, for example, a predetermined measuring apparatus (e.g., a formation tester FMT-MIII manufactured by Nomura Shoji Co., Ltd.). An example of the measuring condition is as follows: calibration sensitivity is 100%; binarization threshold is 0.0%; moving pel is 1; and effective size is 25*18 cm. The measured object can be measured with a face supported by a supporting member during production up. The index of dispersion can be measured by any conventionally known measuring method.

A larger index of dispersion means the lower uniformity of the fabric. In other words, a larger index of dispersion indicates that the high-density regions 11 and the low-density regions 12 are more dispersed in a planar direction, that a difference of absorbance is larger between the high-density regions 11 and the low-density regions 12, and that a difference of density is larger between the high-density regions 11 and the low-density regions 12.

The non-woven fabric 5 of the first embodiment has a property of diffusing a liquid less during transfer and a property of not preventing liquid transfer in a thickness direction since the high-density regions 11 and the low-density regions 12 are dispersedly formed in a planar direction thereof. The non-woven fabric 5 of the first embodiment can be appropriately used for absorbent articles such as disposable diapers and sanitary napkins including a surface sheet which is at least partially liquid permeable, a back sheet which is liquid impermeable, and a liquid retentive absorbent body which is arranged between the surface sheet and the back sheet, as a second sheet arranged between the surface sheet and the absorbent body. The non-woven fabric 5 of the first embodiment can also be appropriately used as a surface sheet of the abovementioned absorbent articles. An absorbing behavior of the non-woven fabric 5 of the first embodiment used as a second sheet of an absorbent article is described below with reference to FIG. 4.

Figure 4:
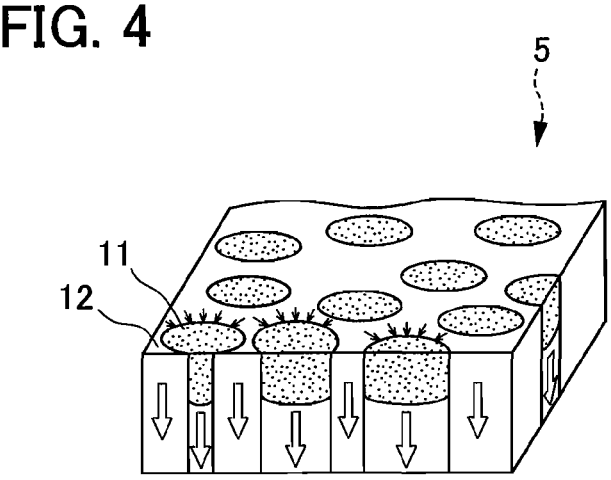
FIG. 4 is a diagram illustrating a low- and high-density structure of the non-woven fabric in the present invention.

As shown in FIG. 4, the high-density regions 11 appropriately draw a thick liquid such as menstrual blood adhered to a top surface (surface sheet side) of the non-woven fabric 5 by capillary action. The low-density regions 12 appropriately transfer the thick liquid such as menstrual blood to a lower part (absorbent body side) of the non-woven fabric 5. The non-woven fabric 5 has the high-density regions 11 and the low-density regions 12 horizontally dispersed, thereby not preventing liquid transfer from a top surface (surface sheet side) to a lower part (absorbent body side) and diffusing a liquid less during transfer. Additionally, the top surface (surface sheet side) does not prevent liquid transfer from the top surface (surface sheet side) to the lower part (absorbent body side).

The low-density regions 12 also have fibers (for example, heat-adhesive fiber 120 which adheres to each other) that are connected to a neighboring high-density region 11. This enables transfer of a liquid accumulated in a surface sheet arranged above a low-density region 12 into a high-density region 11 via fibers of the non-woven fabric 5 arranged as a second sheet. In addition, a liquid such as menstrual blood is transferred to an absorbent body arranged below, without being retained in the high-density region 11 which is composed mainly of synthesized fiber. This enables, for example, maintenance of a property of diffusing a liquid less during transfer and not preventing liquid transfer from a top surface (surface sheet side) to a lower part (absorbent body side), even if a liquid such as menstrual blood is repeatedly discharged to the top surface (surface sheet side).

When the non-woven fabric 5 of the first embodiment is used as a second sheet of an absorbent article, an average density of the non-woven fabric 5 is preferably higher than that of a surface sheet 2, and a density of the high-density region 11 is preferably lower than an average density of an absorbent body 4.

In a case in which the high-density regions 11 are formed dominantly on one side and the low-density regions 12 are formed dominantly on another side of the non-woven fabric 5, a feature thereof as a second sheet differs according to the orientation thereof.

If the side on which the high-density regions 11 are formed dominantly is arranged facing the surface sheet, the second sheet has a property of diffusing a liquid less during transfer and not preventing liquid transfer from the surface sheet to an absorbent body. Contrarily, if the side on which the low-density regions 12 are formed dominantly is arranged facing the surface sheet, even the property of diffusing a liquid less during transfer is elevated.

Thus, by changing the orientation thereof, the non-woven fabric 5 can have different properties. In other words, the non-woven fabric 5 can be used in different orientations in accordance with the application and intended use of an absorbent article 1.

If the side of the second sheet on which the low-density regions 12 are formed dominantly is arranged facing the surface sheet, a liquid on the surface sheet can be promptly transferred to an absorbent body side. If the side on which the low-density regions 12 are formed dominantly is arranged facing the absorbent body, the second sheet can appropriately draw a liquid on the surface sheet and transfer to an absorbent body side.

The second sheet can be prepared with two sheets of the non-woven fabric 5 being laminated. By laminating two sheets of the non-woven fabric 5, a second sheet having different ratios of the low-density regions 12 and the high-density regions 11 and a different arrangement of the high-density regions 11 can be obtained. In this case, a second sheet with unevenness (fiber density gradient) of the low-density regions 12 can be obtained.

The non-woven fabric 5 can also be used folded as a second sheet. In this case, for example, by folding the non-woven fabric 5 with a side on which the high-density regions 11 are formed dominantly facing the inside, the surfaces on which the high-density regions 11 are formed dominantly are made facing each other. Thus, a region for temporarily retaining a liquid transferred from a surface sheet can be made. The region can be made in the same manner when a plurality of sheets of the non-woven fabric 5 is laminated.

A preferred manufacturing method of the non-woven material of the abovementioned embodiment, the first manufacturing method, is described below with reference to FIGS. 5A to 10.

As shown in FIGS. 5A to 5D, the non-woven fabric 5 can be manufactured by heat-processing a fiber web 500 containing a heat-adhesive heat-shrinkable fiber 110 by a predetermined heating device at a temperature at which the heat-shrinkable fiber 110 can be shrunk, then pressing by heat processing a plurality of convex portions 51 formed on one or both sides of the fiber web 500 in a thickness direction.

The first manufacturing method of the non-woven fabric 5 includes: a heat-fusion shrinkage process ST3 in which the fiber web 500 including the heat-adhesive heat-shrinkable fiber 110 is heat-processed at a temperature at which the heat-shrinkable fiber 110 can be melted and shrunk; and a pressing process ST4 in which a plurality of convex portions 51, generated on at least one side of the fiber web by a heat-process in the heat shrinkage process which heat-shrinks the heat-shrinkable fiber 110, is pressed in a thickness direction of the fiber web 500. Each process of the first manufacturing method is hereinafter described in detail with reference to FIG. 6.

In the first manufacturing method, firstly a fiber web 500 of a predetermined thickness is continuously formed by opening, using a carding device, a material (the heat-adhesive heat-shrinkable fiber 110) obtained by blending a first heat-shrinkable fiber 110A and a second heat-shrinkable fiber 110B in an opening process ST1. The fiber web 500 can be formed only by the first heat-shrinkable fiber 110A.

The fiber web 500 includes, for example, a fiber web formed by a carding method and a fiber web formed by an airlaid method. Additionally, to form a non-woven fabric with high-density regions and low-density regions appropriately dispersed, a fiber web is preferably used which is formed by a carding method using comparatively long fibers.

Subsequently, in a feeding process ST2, the fiber web 500 formed in the opening process ST1 is conveyed to an inlet of a heating device 510 by a first conveyer 503 and a second conveyer 505 at a speed S1. In the feeding process ST2, the fiber web 500 is conveyed while being maintained in terms of a degree of freedom between fibers.

Subsequently, in the heat-fusion shrinkage process ST3, the fiber web 500 conveyed in the feeding process ST2 is conveyed in a heating device 510 at a speed S2 by a conveyer 515, and collaterally heat-processed. The fiber web 500 is heat-processed while being supported vertically from below with a lower supporting member having a substantially planate surface 511 (a third conveyer 515), with the heat-shrinkable fiber 110 being restrained from heat-shrinking in a surface supported by the lower supporting member 511. Specifically, the fiber web 500 is heat-processed while being conveyed by the third conveyer 515, by emitting heated air of a predetermined temperature from vertically above. The first heat-shrinkable fiber 110A and the second heat-shrinkable fiber 110B are melted and shrunk at a heating temperature of the heating device 510.

In the heating device 510, hot air is emitted downward from above the fiber web 500 at a temperature at which the first heat-shrinkable fiber 110A and the second heat-shrinkable fiber 110B are melted and shrunk. The fiber web 500 is heated while being pushed against the supporting member 511 with the hot air emitted from above, thus friction between the fiber web 500 and the supporting member 511 is high during the heating process. In other words, heat-shrinkage of the first heat-shrinkable fiber 110A and the second heat-shrinkable fiber 110B, arranged on the supporting member 511-side of the fiber web 500, is suppressed by the friction with the supporting member 511.

Then, the first heat-shrinkable fiber 110A and the second heat-shrinkable fiber 110B arranged on the free surface, not supported by the supporting member 511, of the fiber web 500 are heat-processed virtually without suppression of shrinkage.

Figure 5A:
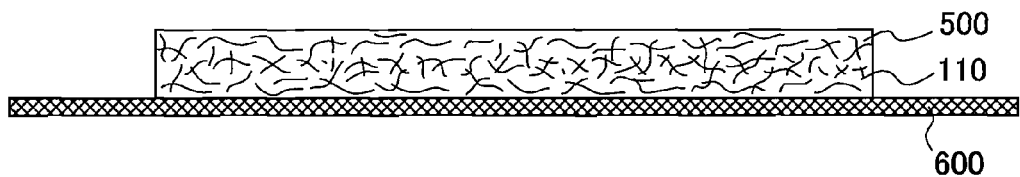
FIG. 5A is a diagram showing an outline of the non-woven fabric manufacturing method of the first embodiment.
Figure 5B:
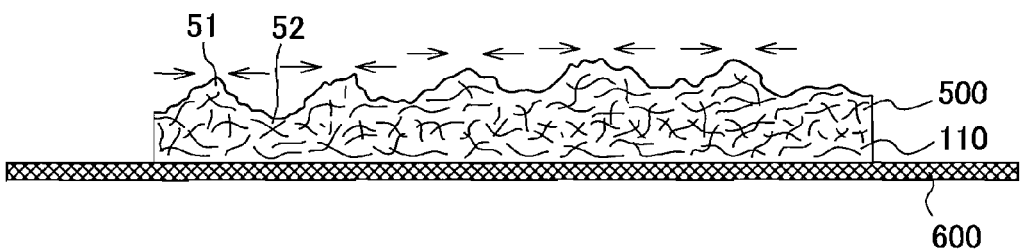
FIG. 5B is a diagram showing an outline of the non-woven fabric manufacturing method of the first embodiment.

As a result, the supporting member 511-side surface of the fiber web is formed substantially planar just as a top surface of the supporting member 511, and on the free surface on the opposite side, a concavo-convex structure (sea-island structure) is formed by the heat-shrinkage of the first heat-shrinkable fiber 110A and the second heat-shrinkable fiber 110B (see FIG. 5B). Here, the first heat-shrinkable fiber 110A and the second heat-shrinkable fiber 110B are melted and adhered to the neighboring fibers by the heat-process in the heat-fusion shrinkage process ST3.

A convex portion 51 (island portion) of the concavo-convex structure is provided by bringing (for example, collecting), in a stretching direction of the first heat-shrinkable fiber 110A and the second heat-shrinkable fiber 110B, a fiber tangled in or arranged in proximity of the first heat-shrinkable fiber 110A and the second heat-shrinkable fiber 110B as the first heat-shrinkable fiber 110A and the second heat-shrinkable fiber 110B are heat-shrunk. In other words, the weight at a position including a convex portion 51 is higher than the average weight of the fiber web 500.

The concave portion 52 (sea portion) is a portion in which fibers are dislocated by the heat-shrinkable fiber 110 and the weight at a position including the concave portion 52 is lower than the average weight.

The temperature of the hot air emitted to the fiber web 500 is preferably 138 to 152° C., and more preferably 142 to 150° C. The velocity of the hot air emitted from above or below to the fiber web 500 is preferably about 1.5 m/s.

In a pressing process ST4, the free surface in which the concavo-convex structure (sea-island structure) is formed is pressed by a roller 700. The roller 700 is arranged to be in contact with the free surface of the fiber web 500, between a first feeding roller 701 and a second feeding roller 703. The fiber web 500 is conveyed in contact with the roller 700 by virtue of the tension.

Figure 5C:
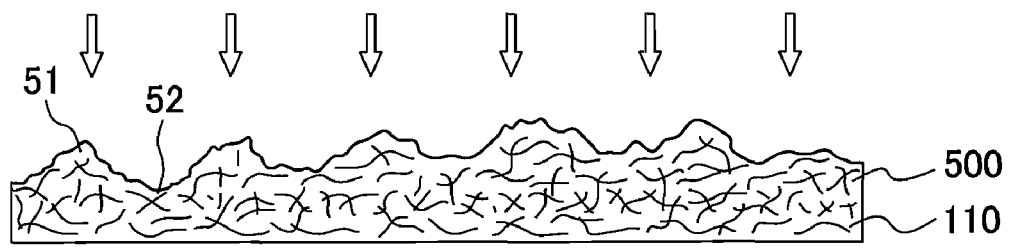
FIG. 5C is a diagram showing an outline of the non-woven fabric manufacturing method of the first embodiment.
Figure 5D:
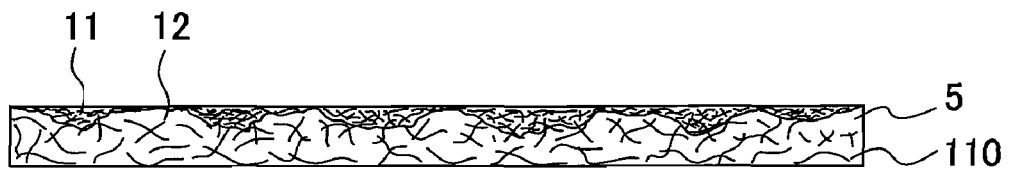
FIG. 5D is a diagram showing an outline of the non-woven fabric manufacturing method of the first embodiment.

Then, a plurality of convex portions 51 formed on the free surface of the fiber web 500 is continuously pressed in a thickness direction by the roller 700 (see FIGS. 5C and 5D).

The roller 700 is preferably heated to a predetermined temperature. The roller 700 heated to the predetermined temperature while being in contact with the free surface of the fiber web 500 appropriately presses in a thickness direction the convex portions 51 formed on the free surface.

In a pressing process ST4, the plurality of convex portions 51 formed on the free surface of the fiber web 500 is pressed in a thickness direction by the roller 700 and a plurality of high-density regions 11 is formed on the free surface. Furthermore, in the pressing process ST4, the convex portions 51 dispersedly formed in a planar direction of the non-woven fabric 5 are pressed and a plurality of high-density regions 11 is dispersedly formed in the planar direction.

Since the fiber web 500 is pressed against the roller 700 with a constant intensity, the non-woven fabric 5 has a substantially even thickness.

Figure 6:
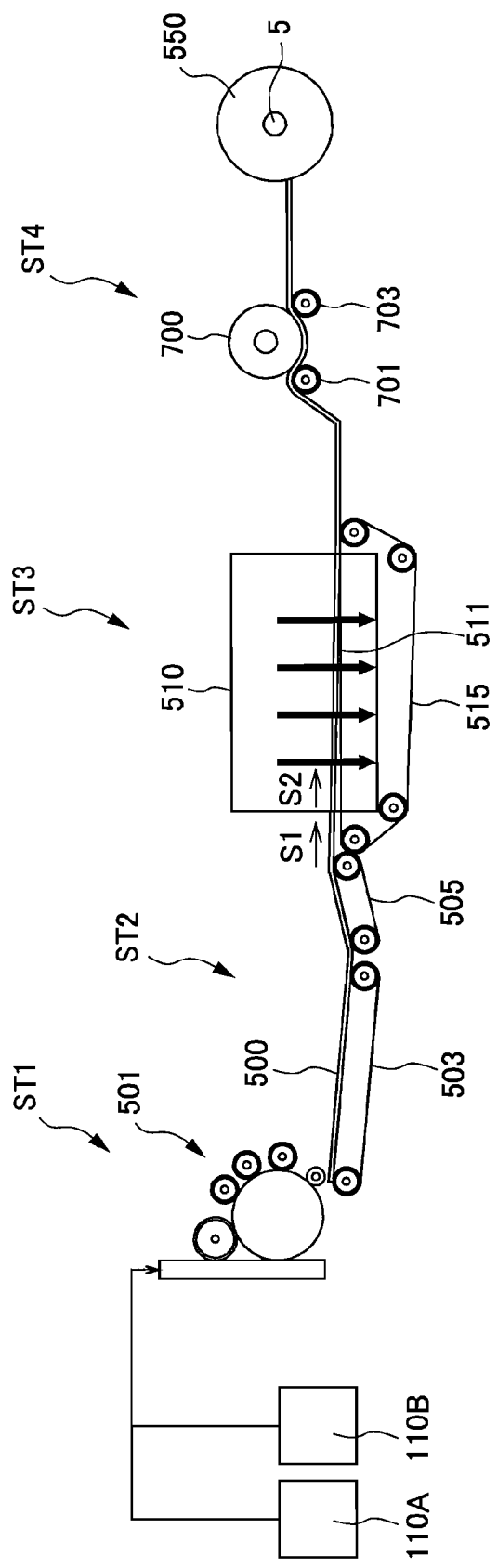
FIG. 6 is a diagram showing a non-woven fabric manufacturing method of the first embodiment.

Subsequently, a pressing method different from that of FIG. 6 is hereinafter described with reference to FIGS. 7 to 10.

Figure 7:
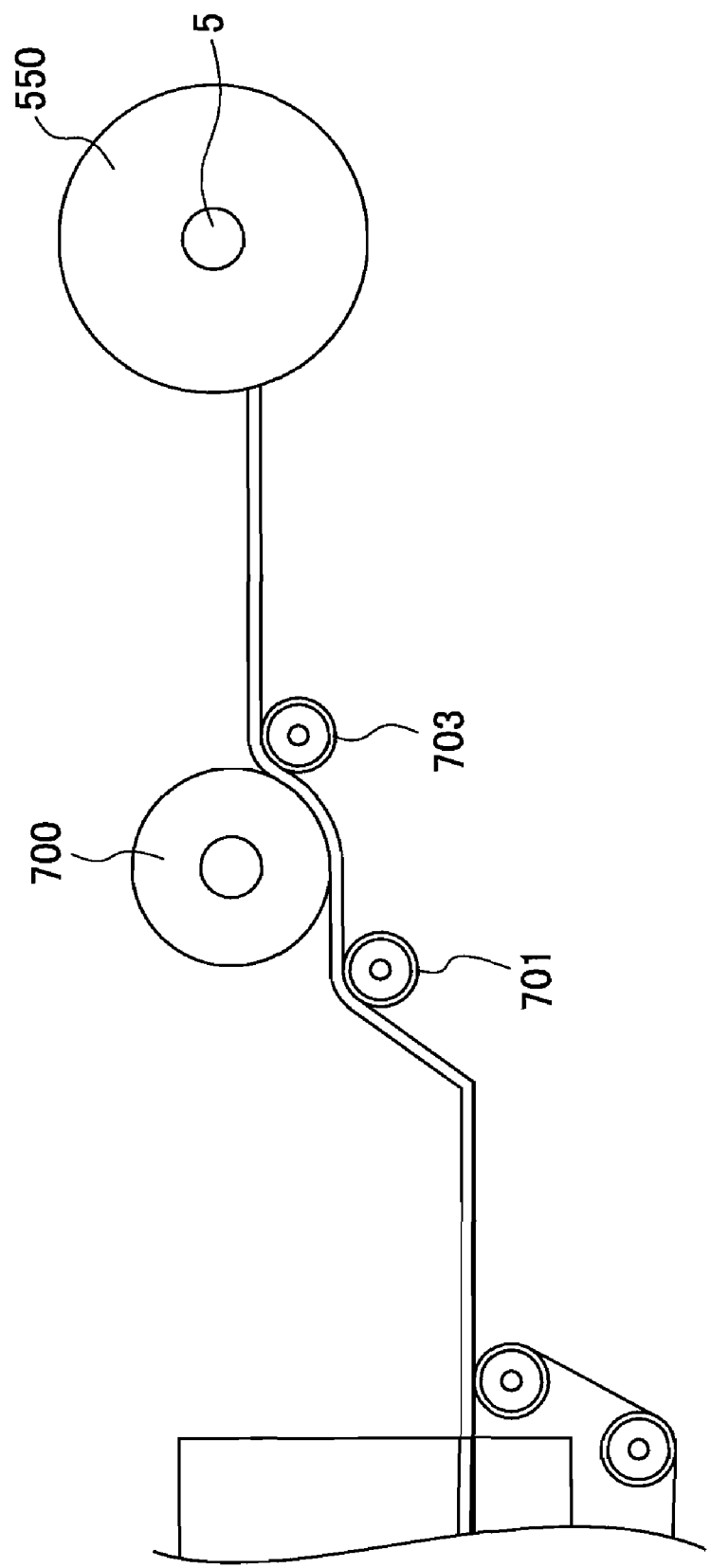
FIG. 7 is a diagram showing another embodiment of the pressing process in the manufacturing method shown in FIG. 6.

In the pressing method shown in FIG. 7, as in the pressing method shown in FIG. 6, the roller 700 being in contact with the free surface of the fiber web 500 presses the convex portions in a thickness direction. In FIG. 7, by adjusting the placement of the second feeding roller 703, the free surface of the fiber web 500 is brought into contact with the roller 700, to the second feeding the roller 703-side. In other words, by adjusting the placement of the first feeding roller 701, the second feeding roller 703, and the roller 700, the fiber web 500 is brought into contact with the roll 700 only by virtue of the tension, and convex portions are pressed to form high-density regions.

Figure 8:
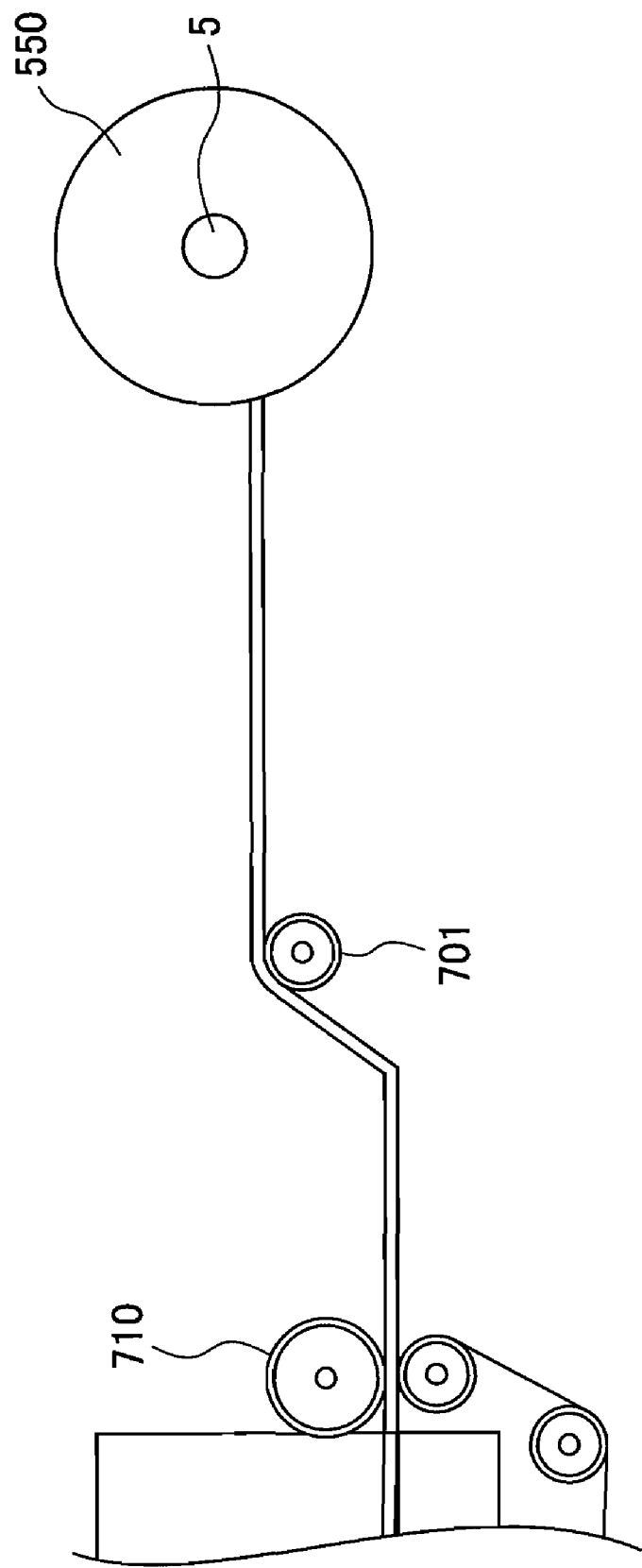
FIG. 8 is a diagram showing another embodiment of the pressing process in the manufacturing method shown in FIG. 6.

Alternatively, as shown in FIG. 8, by arranging a roller 710 in the vicinity of an outlet of the heating device 510 and bringing the free surface of the fiber web 500, just from the heating device 510 and still at a predetermined temperature, into contact with the roller 710, a plurality of the convex portions 51 on the free surface can be pressed in a thickness direction.

In this case, the convex portions 51 can be pressed in a thickness direction before the first heat-shrinkable fiber 110A and the second heat-shrinkable fiber 110B are completely adhered and fixed; the free surface is thus formed to be more planar.

Figure 9:
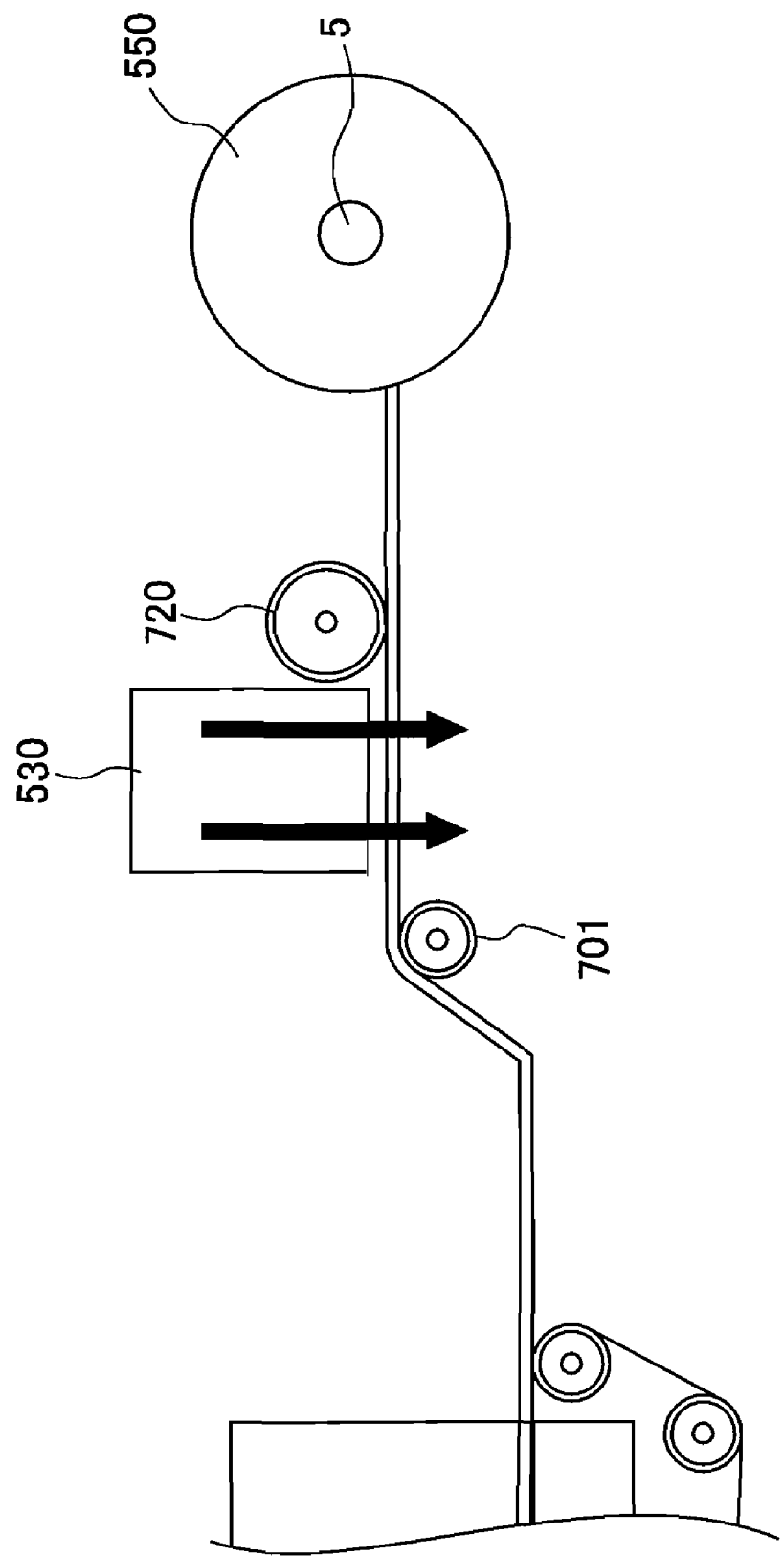
FIG. 9 is a diagram showing another embodiment of the pressing process in the manufacturing method shown in FIG. 6.

Alternatively, as shown in FIG. 9, the fiber web 500 can be reheated by a heating device 530, and then the free surface thereof can be pressed by a roller 720. For example, the fiber web 500 with a concavo-convex structure (sea-island structure) formed on the free surface can be heated in the heating device 530 by emitting hot air at a predetermined temperature to make the convex portions 51 easily compressible, then the convex portions 51 are pressed by the roller 720. As a result, the convex portions 51 formed on the free surface of the fiber web 500 are appropriately pressed and form the high-density regions 11.

Figure 10:
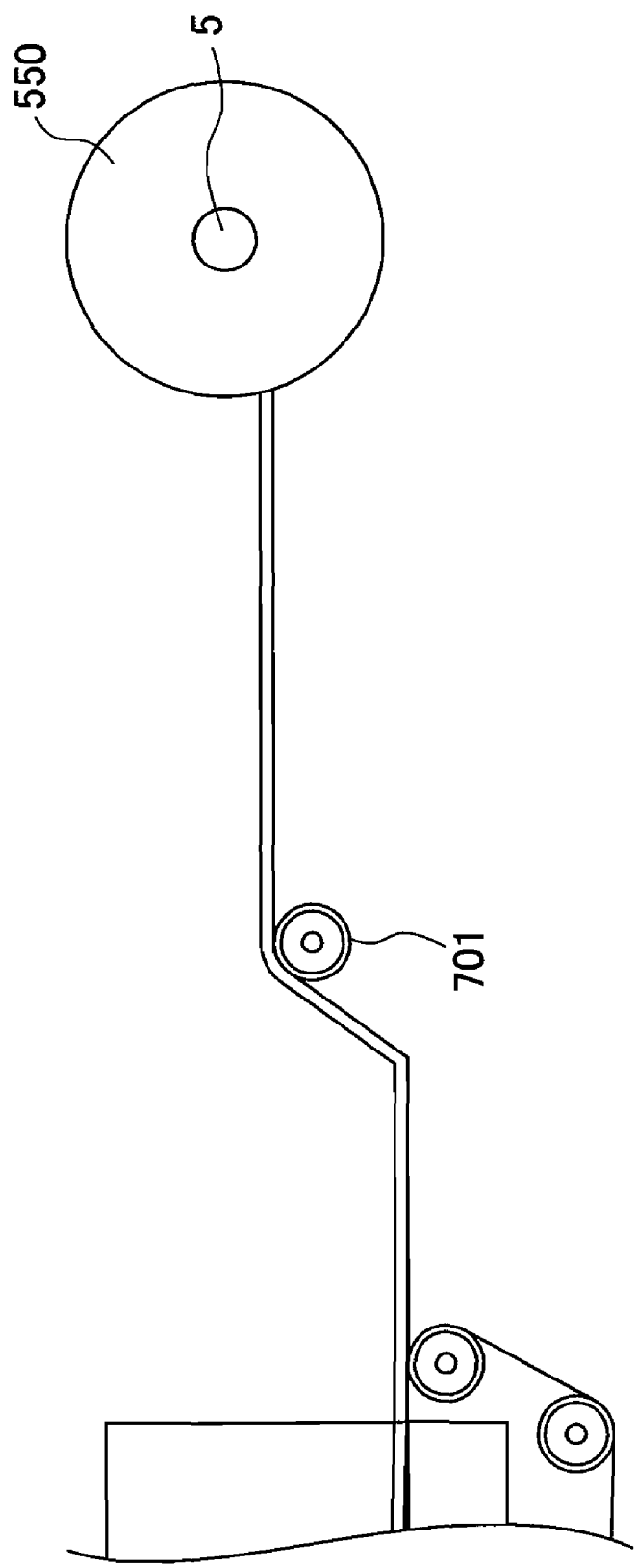
FIG. 10 is a diagram showing another embodiment of the pressing process in the manufacturing method shown in FIG. 6.

Alternatively, as shown in FIG. 10, by reeling the non-woven fabric 5 (the fiber web 500) by a wind-up portion 550 and laminating the non-woven fabric 5 in a radial direction, without pressing with a roller or the like, a plurality of the convex portions 51 formed on the free surface of the fiber web can be pressed in a thickness direction. Specifically, since the side supporting the fiber web 500 of the supporting member 511 is substantially planar, the free surface having the concavo-convex structure (sea-island structure) is entirely pressed by a surface formed to be planar. This method can produce a non-woven fabric 5 of substantially even thickness without a pressing means such as roller.

In this case, a heating process (not shown) heating the fiber web 500 at a predetermined temperature is preferably provided before the process reeling the fiber web 500 with the wind-up portion 550. By providing the heating process, the non-woven fabric 5 can be reeled with the first heat-shrinkable fiber 110A and the second heat-shrinkable fiber 110B being heated and easy to transform, and thus the convex portions 51 formed on the free surface can be appropriately pressed in a thickness direction.

In addition, in the heating device 510, by heat-processing the fiber web 500 being arranged between an air permeable supporting member 511 and another air permeable supporting member (not shown) arranged vertically above and substantially parallel to the supporting member 511, the concavo-convex structure (sea-island structure) can be formed in both sides of the fiber web 500.

For example, by emitting heated air of a predetermined temperature from vertically below the supporting member 511 and emitting heated air of a predetermined temperature from vertically above a supporting member arranged above (not shown), the fiber web 500 can be heat-processed while being partially or entirely spaced apart from the supporting member 511 and/or the supporting member arranged above (not shown).

In this case, the hot air is emitted from both above and below fiber web 500. The fiber web 500 can be heat-processed being entirely spaced apart from the supporting member 511 and/or the supporting member arranged above (not shown), by emitting the hot air from above and below alternately. As a result, a friction between the fiber web 500 and the supporting member 511 and the supporting member arranged above (not shown) is reduced, and thus the fiber web 500 can be heat-processed without being inhibited in terms of shrinkability.

Another preferred manufacturing method of the non-woven fabric 5 of the first embodiment, the second manufacturing method, is described below with reference to FIG. 11. The second manufacturing method includes: a first process ST3a in which the heat-fusion shrinkage process ST3 forms a plurality of convex portions in one or both sides of the fiber web 500 by shrinking a heat-shrinkable fiber; and a second process ST3b in which the plurality of convex portions formed in the first process ST3a is pressed in a thickness direction of the fiber web 500. In other words, in the second manufacturing method, the heat-fusion shrinkage process ST3 and the pressing process ST4 of the first manufacturing method are included in the heat-fusion shrinkage process ST3. It should be noted that the opening process ST1 and the feeding process ST2 of the second manufacturing method are the same as that of the first manufacturing method. The heat-fusion shrinkage process ST3 of the second manufacturing method is mainly described hereinafter.

Figure 11:
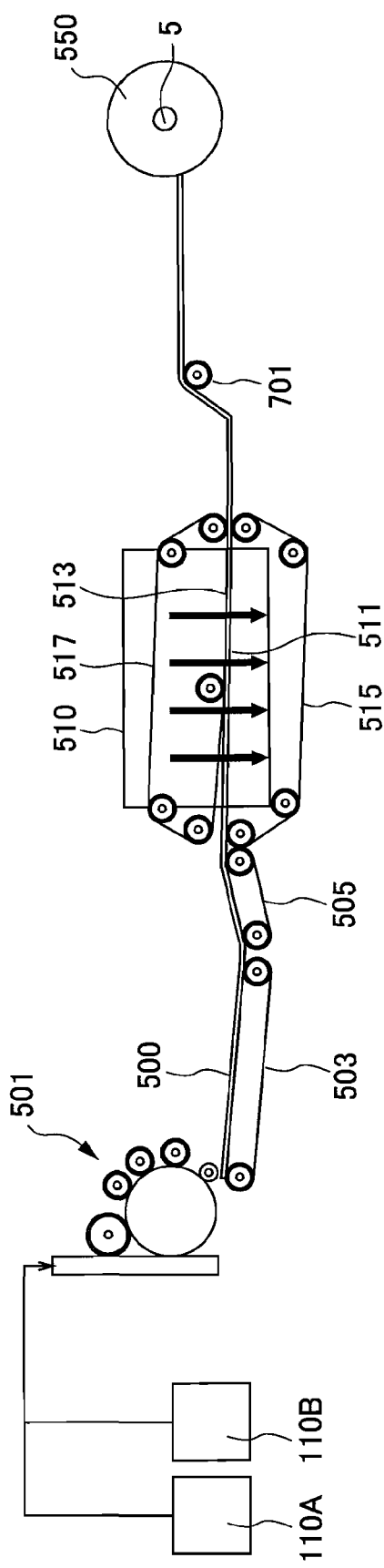
FIG. 11 is a diagram showing another embodiment of the non-woven fabric manufacturing method of the first embodiment.

In the heat-fusion shrinkage process ST3 of the second manufacturing method, as shown in FIG. 11, in an anterior part of the heating device 510, a third upper conveyer 517 (an upper supporting member 513) is arranged to form a predetermined angle with a horizontal direction and at a predetermined distance away from a top surface of the fiber web 500. Then, in a posterior part of the heating device 510, the upper supporting member 513 is arranged parallel to the horizontal direction and in contact with the top surface of the fiber web 500. A third lower conveyer 515 (a lower supporting member 511) is arranged parallel to the horizontal direction and supports the fiber web 500 from below, from an inlet to an outlet of the heating device 510.

The fiber web 500 fed into the abovementioned heating device 510 is, in the anterior part thereof, conveyed with a lower surface supported by the lower supporting member 511, and has a top surface heated with hot air emitted from above an upper supporting member 513 and passing through the upper supporting member 513. In other words, the fiber web 500 is heated with the lower surface supported by (contacting) the lower supporting member 511 and with the top surface not contacting the upper supporting member 513. By heating in the abovementioned arrangement, as stated above, heat-shrinkage of the first heat-shrinkable fiber 110A and the second heat-shrinkable fiber 110B is suppressed by the friction, and a plurality of convex portions are formed on the top surface (free surface) (the first process ST3a).

Then, in the posterior part of the heating device 510, the fiber web 500 is conveyed while being wedged between the lower supporting member 513 and the upper supporting member 513. In other words, in the anterior part of the heating device 510, a plurality of convex portions 51 formed on the top surface of the fiber web 500 is pressed in a thickness direction thereof by the lower supporting member 511 and the upper supporting member 513. As a result, the plurality of convex portions 51 is pressed in a thickness direction and a plurality of high-density regions 11 is formed on the top surface of the fiber web 500 (non-woven fabric 5) (the second process ST3b).

In a description of the first and the second manufacturing method, the fiber web 500 is heat-shrink processed while being supported by the lower supporting portion 511; however, the invention is not limited thereto. The fiber web 500 can be heated, for example, with the lower surface spaced apart from the lower supporting member 511 by emitting hot air from vertically below the lower supporting member 511. In other words, by thus heat-processing the fiber web 500 and forming a plurality of convex portions on both surfaces thereof, then pressing the plurality of convex portions 51 in a thickness direction, a non-woven fabric 5 with a plurality of high-density regions 11 on both of the surfaces can be produced.

Figure 12:
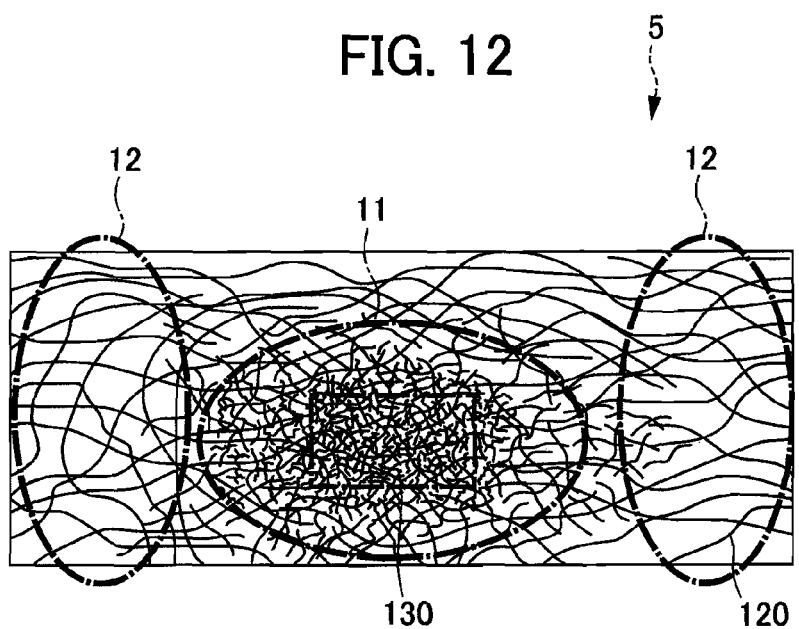
FIG. 12 is a cross-sectional view showing a non-woven fabric in the second embodiment.
Figure 13:
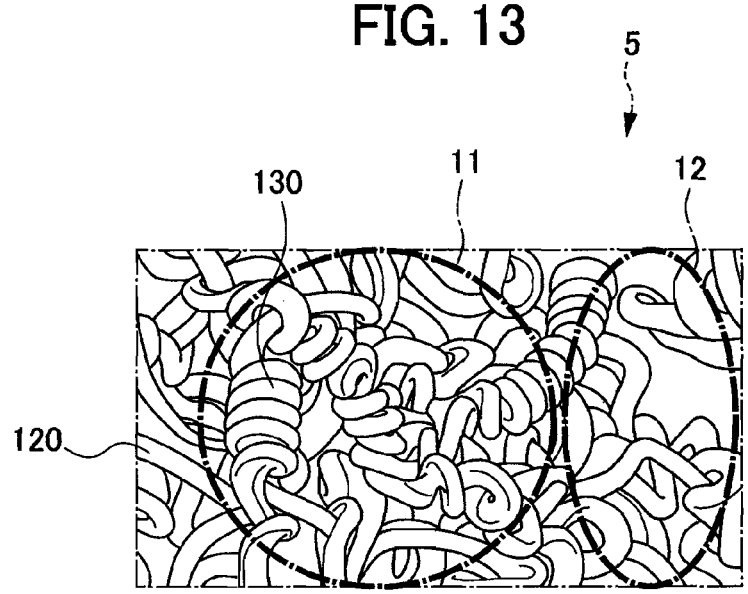
FIG. 13 is a partially enlarged view of FIG. 12.

The second embodiment of the non-woven fabric 5 of the present invention is described below with reference to FIGS. 12 and 13. Differences from the first embodiment are mainly described below. The same components and parts as those of the first embodiment are designated by the same numerals, and hence the detailed description is not repeated. Unless otherwise described, the descriptions for the first embodiment apply. The non-woven fabric of the second embodiment is different from that of the first embodiment in that, as shown in FIGS. 12 and 13, fibers constituting a non-woven fabric 5 include a heat-adhesive fiber 120 and a heat-shrinkable fiber 130 having crimpability at least when heat-shrunk. Moreover, in the second embodiment, the high-density regions 11 are composed mainly of a heat-shrinkable fiber 130 heat-shrunk and the low-density regions 12 are composed mainly of the heat-adhesive fiber 120 adhered to each other.

Examples of the heat-shrinkable fiber 130 include an eccentric sheath-core type composite fiber consisting of two thermoplastic polymer materials of different shrinkage ratios, and a side-by-side composite fiber. Examples of a pair of thermoplastic polymer materials of different shrinkage ratio include a combination of ethylene-propylene random copolymer and polypropylene, a combination of polyethylene and ethylene-propylene random copolymer, and a combination of polyethylene and polyethylene terephthalate. Specific examples are EP manufactured by Chisso Corporation, MSW manufactured by Toyobo Co., Ltd. and CPP manufactured by Daiwabo Co., Ltd. For example, a heat-shrinkable fiber having potential crimpability is preferred.

The heat-shrinkable fiber 130 is, for example, a short staple fiber of which length is preferably 5 to 90 mm and thickness is preferably 1 to 11 dtex.

Examples of the heat-shrinkable fiber 120 include a fiber composed of polyethylene (PE), polypropylene (PP), and polyethylene terephthalate (PET). A fiber composed of ethylene-polypropylene copolymer, polyester, and polyamide can also be used. A sheath-core type composite fiber consisting of a combination of the abovementioned thermoplastic polymer materials and a side-by-side composite fiber can also be used.

The heat-adhesive fiber 120 is, for example, a short staple fiber of which length is preferably 5 to 90 mm and thickness is preferably 1 to 11 dtex.

Regarding the mixing ratio of the heat-shrinkable fiber 130 and the heat-adhesive fiber 120, the ratio of the heat-shrinkable fiber 130 is preferably 10 to 90% by mass, and more preferably 30 to 70% by mass with respect to the total fiber amount. In a case in which the ratio of the heat-shrinkable fiber 130 is in the abovementioned range, the high-density regions 11 and the low-density regions 12, are appropriately provided by bringing (for example, collecting), in a stretching direction of the heat-shrinking fiber 110, a heat-shrinkable fiber 120 tangled in or arranged in proximity of the heat-shrinking fiber 130 as the heat-shrinkable fiber 130 is heat-shrunk.

A ratio of the heat-adhesive fiber 120 is preferably no more than 90% by mass, and more preferably no more than 70% by mass with respect to the total fiber amount of the non-woven fabric 5. In a case in which the ratio of the heat-adhesive fiber 120 is in the abovementioned range, the heat-adhesive fiber 120 can have a large enough number of junctions, and a networking structure can be appropriately provided. Since the heat-adhesive fiber 120 can have a large enough number of junctions, the non-woven fabric 5 can maintain the tensile strength during a manufacturing process and an additional process for producing absorbent articles therefrom.

A heat shrinkage ratio of the heat-shrinkable fiber 130 at a predetermined temperature (145° C. for example) is preferably more than 10%, and more preferably 20 to 80%.

The heat-adhesive fiber 120 does not have heat-shrinkability, or have shrinkability no more than 10%, and preferably no more than 7%, at the predetermined temperature (145° C. for example). In a case in which the heat-shrinkable fiber 130 and the heat-adhesive fiber 120 have the abovementioned heat-shrinkage ratio, the high-density regions 11 and the low-density regions 12 are appropriately formed. In other words, by heating at a predetermined temperature a fiber web composed of fibers of different heat-shrinkage ratios, a non-woven fabric can be obtained with high-density regions 11 and low-density regions 12 dispersedly formed in a planar direction.

Additionally, the heat-shrinkable fiber 130 can be shrunk at a higher temperature than the temperature at which the heat-adhesive fiber 120 can be melted. A temperature at which the heat-shrinkable fiber 130 can be shrunk is preferably higher by at least 5° C., and more preferably by at least 10° C. more than the temperature at which the heat-adhesive fiber 120 can be melted. In this case, a networking structure can be formed, for example, by heat-processing at a temperature at which the heat-adhesive fiber 120 can be melted and the heat-shrinkable fiber 130 cannot be shrunk.

Even more particularly, since the temperature at which the heat-shrinkable fiber 130 can be melted is higher than the heat-shrinkage temperature thereof, the heat-shrinkable fiber 130 being heat-shrunk which constitutes the high-density regions 11 is adhered to the heat-adhesive fiber 120 at the junction thereto; however, the heat-shrinkable fibers 130 are not substantially adhered to each other. In other words, by heat-processing a fiber web 500 on which a networking structure is formed at a temperature at which the heat-shrinkable fiber 130 can be shrunk but not be melted, the heat-shrinkable fiber 130 is crimped tangling other fibers, and high-density regions 11 and low-density regions 12 can be formed.

In the second embodiment, an index of dispersion, in a planar direction of the high-density regions 11 and the low-density regions 12 of the non-woven fabric 5 is preferably 250 to 790, and more preferably 310 to 705.

When the index of dispersion is smaller than 250, the concavo-convex structure becomes nearly even. Consequently, a property of the low-density regions 12 diffusing a liquid less during transfer and a property of the high-density regions 11 not preventing liquid transfer in a thickness direction of the non-woven fabric may not be provided at the same time. When the index of dispersion is larger than 790, the concavo-convex structure becomes too uneven and a liquid temporarily captured in the low-density regions 12 cannot be transferred to the high-density regions 12. Consequently, a property of the low-density regions 12 diffusing a liquid less during transfer and a property of the high-density regions 11 not preventing liquid transfer in a thickness direction of the non-woven fabric may not be provided at the same time.

A preferred manufacturing method of the non-woven fabric 5 of the second embodiment, the third manufacturing method, is described below with reference to FIGS. 14 and 15. A preferred manufacturing method of the non-woven fabric 5 of the second embodiment, the third manufacturing method, includes: an opening process ST1, a feeding process ST2, a heat-fusion process ST5, and a heat-shrinkage process ST6. Each process is described hereinafter. The opening process ST1 and the feeding process ST2 of the third manufacturing method are similar to that of the first manufacturing method except that a heat-adhesive fiber 120 and a heat-shrinkable fiber 130 are used in place of the first heat-shrinkable fiber 110A and the second heat-shrinkable fiber 110B.

In the heat-fusion process ST5, the fiber web 500 conveyed in the feeding process ST2 is conveyed in a heating device 510 at a speed S2 by a conveyer 515, and heat fusion treated. Specifically, the fiber web 500 is heat-processed while being conveyed by the third conveyer 515, by emitting heated air of a predetermined temperature from vertically above. The heat-adhesive fiber 120 is melted and the heat-shrinkable fiber 130 is not substantially shrunk at a heating temperature of the heating device 510. This makes the heat-adhesive fiber 120 of the fiber web 500 adhered to each other and a networking structure is formed. In other words, in the heat-fusion process ST5, mainly the heat-adhesive fiber 120 of the fiber web 500 is adhered to each other as a temporary bond.

In the heating device 510, hot air is emitted downward from above the fiber web 500 at a temperature at which the heat-adhesive fiber 120 can be melted and the heat-shrinkable fiber 130 is not substantially shrunk. The fiber web 500 is heated while being pushed against the supporting member 511 (a third conveyer 515) with the hot air emitted from above, and thus friction between the fiber web 500 and the supporting member 511 is high during the heat-fusion process. This makes the heat-adhesive fiber 120 of the fiber web 500 adhere to each other, with a shrinkage of the fiber web 500 being inhibited, and a networking structure is formed.

In the heat-shrinkage process ST6, the fiber web 500, heat-adhered in the heat-fusion process ST5 is conveyed in a second heating device 520 at a speed S3 by a fourth lower conveyer 525, and heat-shrunk processed.

In the heat-shrinkage process ST6, the second heating device 520 heat-shrinks the heat-adhered fiber web 500, conveying to a predetermined direction by the fourth lower conveyer 525, at a temperature at which the heat-shrinkable fiber 130 contained therein can be heat-shrunk. In other words, the fiber web 500, with a networking structure is formed thereon and shrinkage thereof is inhibited, and is heat-processed so that the heat shrinkable fiber 130 is heat-shrunk.

By heat-shrinking the heat shrinkable fiber 130 when a networking structure is formed and shrinkage is inhibited on the fiber web 500, high-density regions 11 and low-density regions 12 can be formed. Specifically, the high-density regions 11 and the low-density regions 12 are appropriately formed by dislocating a heat-shrinkable fiber 120 and the like tangled in or arranged in proximity of the heat-shrinking fiber 130 to a stretching direction of the fiber web 500 as the heat-shrinkable fiber 130 is heat-shrunk. In other words, the high-density regions 11 formed by shrinkage and accumulated heat-shrinkable fibers 130 and the low-density regions 12, in which fibers are not dislocated by the shrinkage of the heat-shrinkable fiber 130 due to the networking structure formed by junctions of the heat-adhesive fiber, can be mixed.

The processing temperature of the heat-shrinkage process ST6 is higher than that of the heat-fusion process ST5. This owes to the fact that the heat-shrinkable fiber 130 can be shrunk at a higher temperature than the temperature at which the heat-adhesive fiber 120 can be melted. The processing temperature of the heat-shrinkage process ST6 is higher by at least 5° C., and preferably by at least 10° C. higher than that of the heat-fusion process ST5.

The heating process of the heat-shrinkage process ST6 in the second heating device 520 is performed preferably with little friction between the fiber web 500 and the lower supporting member 525 and the like, in order to avoid inhibition of the shrinkability of the fiber web 500.

Figure 14:
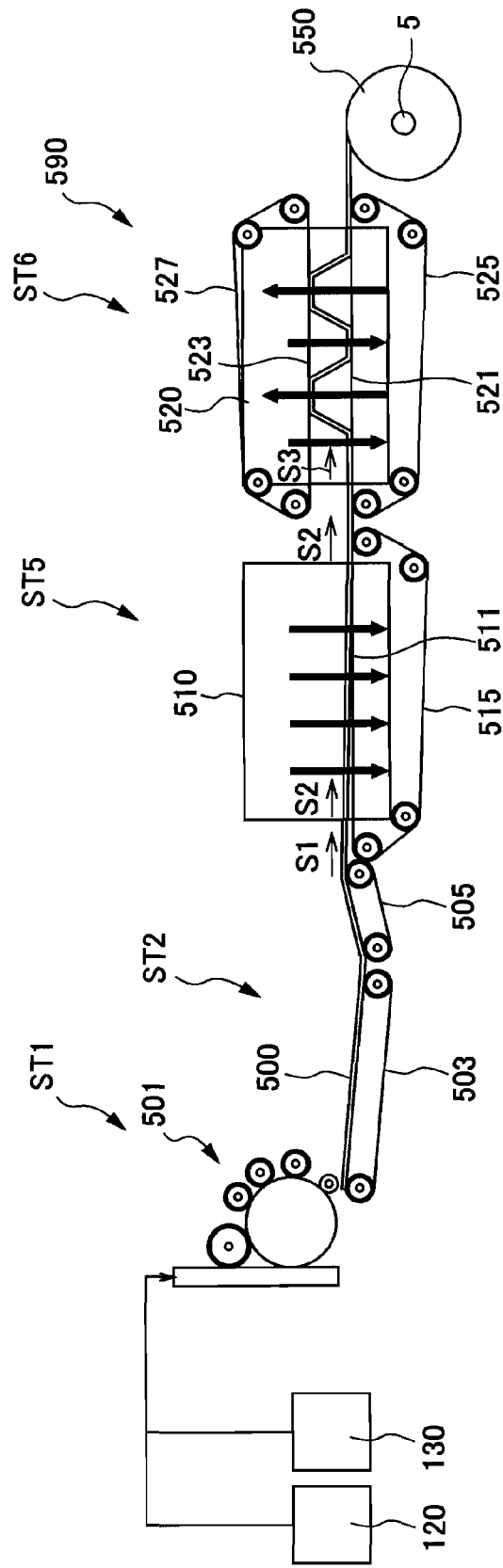
FIG. 14 is a diagram showing a non-woven fabric manufacturing method of the second embodiment.

In the second heating device 520, the fiber web 500 is conveyed while being arranged between the fourth lower conveyer 525 and the fourth upper conveyer 527 as shown in FIG. 14. Here, the fourth lower conveyer 525 is a lower supporting member 521 which is an air-permeable first supporting member, and the fourth upper conveyer 527 is an upper supporting member 523 which is an air-permeable second supporting member which is arranged vertically above and substantially parallel with a predetermined distance away from a lower supporting member 521. Then, by emitting heated air of a predetermined temperature from vertically below the supporting member 511 and emitting heated air of a predetermined temperature from vertically above the upper supporting member 523, the fiber web 500 can be heat-processed while being partially or entirely spaced apart from the lower supporting member 521 and/or the upper supporting member 523.

In this case, the hot air is emitted from both above and below the fiber web 500. The fiber web 500 can be heat-processed while being entirely spaced apart from the lower supporting member 521 and/or the upper supporting member 523, by emitting the hot air from above and below alternately. As a result, friction between the fiber web 500 and the lower supporting member 521 and the upper supporting member 523 is reduced, and thus the fiber web 500 can be heat-processed without being inhibited in terms of shrinkability.

Here, the temperature of the hot air is preferably 100 to 160° C., and more preferably 120 to 140° C. The speed of the hot air emitted from above is preferably 4 to 13 m/s, and more preferably 7 to 10 m/s; the speed of the hot air emitted from below is preferably 4 to 13 m/s, and more preferably 7 to 10 m/s.

The heating process of the heat-shrinkage process ST6 in the second heating device 520 is performed preferably to the fiber web 500 while being slack, in order to avoid inhibition of the shrinkability of the fiber web 500.

Figure 15:
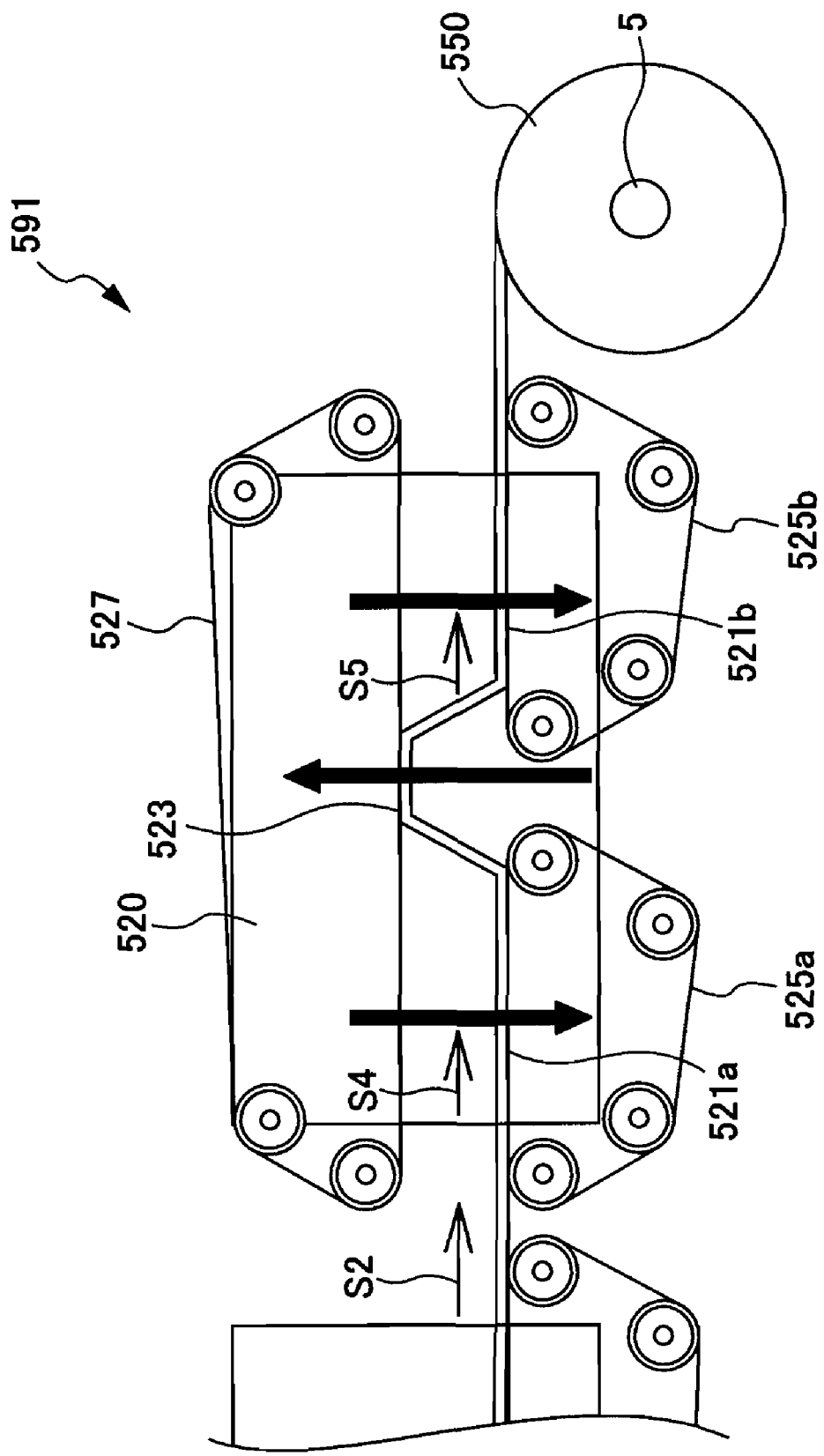
FIG. 15 is a diagram showing another embodiment of the heat-shrinkage process in the manufacturing method shown in FIG. 14.

Additionally, in the heat-shrinkage process ST6, the fourth lower conveyer 525 of the second heating device 520 can be divided into an anterior conveyer 525a and a posterior conveyer 525b that can be serially arranged in a feeding direction at a predetermined distance away from each other, as shown in FIG. 15. By keeping an area between the anterior conveyer 525a and the posterior conveyer 525b free from a supporting member and the like, and emitting hot air thereon from below the fiber web, a region virtually free of friction can be formed on the fiber web 500. In addition, by heat-processing the fiber web 500 while being slack, the inhibition of shrinkability of the fiber web 500 (especially shrinkability inhibition in a feeding direction) can be avoided more effectively. The fiber web 500 can be slacked by, for example, adjusting the feeding speed of the posterior conveyer 525b to be lower than that of the anterior conveyer 525a.

In the second heating device 520 including the anterior conveyer 525a and the posterior conveyer 525b, as shown in FIG. 15, firstly hot air is emitted from above to the fiber web 500 while being supported and conveyed by the anterior conveyer 525a (an anterior lower supporting member 521a). Subsequently, in the area free of any supporting member, hot air is emitted from below to the fiber web 500. Then, the fiber web 500 is supported by or spaced from the fourth upper conveyer 527 (the upper supporting member 523), and conveyed toward the posterior conveyer 525b. Thereafter, the fiber web 500 is supported and conveyed by the posterior conveyer 525b (a posterior lower supporting member 521b) while being heated by hot air emitted from above. The inhibition of shrinkability of the fiber web 500 is thus appropriately avoided and the high- and low-density regions are appropriately formed on the non-woven fabric 5.

A ratio of the feeding speed S3 of the fiber web 500 in the heat shrinkage process to the feeding speed S2 of the fiber web 500 in the heat-fusion process ST6 can be adjusted to be larger than a heat-shrinkage ratio of the fiber web 500 at the heat-process temperature in the heat shrinkage process ST6 of the fiber web 500 being conveyed by the feeding process ST2. In other words, the fiber web 500, being heat-processed in the heat-fusion process and with a networking structure formed thereon, is heat-processed in the heat-shrinkage process with inhibition of the shrinkage. Here, the feeding speeds S2 and S3 can be adjusted in accordance with, for example, the heat-shrinkage ratio of the heat-shrinkable fiber 130 at the heating temperature of the heat-shrinkage process ST6. The heat-shrinkage ratio indicates a length after the heat-shrinkage with respect to a length before the heat-shrinkage, in the free state.

In the third manufacturing method, the heat-fusion process takes place in the first heating device 510 and the heat-shrinkage process in the second heating device; however, these processes can take place in the same device. For example, in a non-woven fabric manufacturing device 590 shown in FIG. 14, the first heating device 510 can be omitted and the heating process can take place in the second heating device 520 at a temperature at which the heat-shrinkable fiber 130 can be shrunk.

In this case, a feeding speed S3 of the fiber web in the heat-shrinkage process ST6 is adjusted so that a ratio of the feeding speed S3 to the feeding speed S2 of the fiber web 500 in the feeding process is larger than a heat-shrinkage ratio of the fiber web 500 at the heating temperature in the heat shrinkage process ST6. In other words, the fiber web 500 composed of the heat-shrinkable fiber 130 and the heat-adhesive fiber 120 being mixed is heat-processed in the heat-shrinkage process ST6 with inhibition of the shrinkage. Here, the feeding speeds S2 and S3 can be adjusted in accordance with, for example, the heat-shrinkage ratio of the heat-shrinkable fiber 130 and the heat-adhesive fiber 120 at the heating temperature of the heat-shrinkage process ST6.

A pre-heating process (not shown) can be included prior to the heat-adhesive process ST5, in which the fiber web is heated to limit a degree of freedom of the heat-shrinkable fiber 130 by thinning a thickness of the fiber web 500. In the pre-heating process, heat-processing is preferably performed at a temperature at which the heat-adhesive fiber 120 is not substantially melted and the heat-shrinkable fiber 130 is not substantially shrunk.

EXAMPLES

The present invention is described in detail hereafter by examples and comparative examples. It should be noted that the present invention is not limited thereto.

Examples 1 to 4

The non-woven fabric of Examples 1 to 4 and Comparative Examples 1 and 2 were produced according to the above-mentioned first manufacturing method. Physical properties of textile materials used for the Examples and Comparative Examples are shown in following Table 1. It should be noted that a card machine was operated at the rate of 20 m/min in the opening process ST1. In the feeding process ST2, the fiber web of 300 mm*300 mm was conveyed. In a heat-adhesive shrinkage process, a conveyer consisting of an air permeable net (20 mesh) was used and a fiber web was conveyed with a feeding speed of 3 m/min. In a heating device, hot air of 145° C. and of wind velocity 0.7 m/s was emitted downward from above.

The non-woven fabric of Examples 1 to 4 and Comparative Examples 1 and 2 was thus obtained. The non-woven fabric of Examples 1 to 4 has high-density regions being formed dominantly on one side. The non-woven fabric of Example 1 is an ultra-high density sheet composed solely of a heat-adhesive fiber, having a substantially even crude density in a planar direction. The non-woven fabric of Example 2 is an ultra-low density sheet composed solely of a heat-adhesive fiber, having an even crude density in a planar direction.

Example 5

The non-woven fabric of Example 5 was produced by laminating two sheets of the non-woven fabric of Example 2.

Example 6

The non-woven fabric of Example 6 was produced by laminating three sheets of the non-woven fabric of Example 2.

[Measurement of the Mixture Ratio (Degree of Dispersion) of High-Density Regions and Low-Density Regions]

The index of dispersion was measured for non-woven fabrics of Examples 1 to 6 and Comparative Examples 1 and 2. Table 1 shows the results of the measurement.

TABLE 1

| Sample | Fiber property | Material (Core/Sheath) | Core/Sheath ratio | Fiber diameter (T) | fiber length (mm) | Web shrinkage ratio at 145° C. (%) | Mixture ratio (%) | Weight (g/m2) | Standard deviation |
|---|---|---|---|---|---|---|---|---|---|
| Example 1 | Heat-shrinkable fiber | PE/PET | 40/60 | 4.4 | 32 | 20 | 70 | 30 | 287 |
| | Heat-shrinkable fiber | PE/PET | 40/60 | 2.8 | 51 | 30 | 30 | | |
| Example 2 | Heat-shrinkable fiber | PE/PET | 40/60 | 4.4 | 32 | 20 | 70 | 30 | 368 |
| | Heat-shrinkable fiber | PE/PET | 40/60 | 2.8 | 32 | 30 | 30 | | |
| Example 3 | Heat-shrinkable fiber | PE/PET | 40/60 | 6.0 | 51 | 20 | 50 | 30 | 320 |
| | Heat-shrinkable fiber | PE/PET | 40/60 | 2.8 | 51 | 30 | 50 | | |
| Example 4 | Heat-shrinkable fiber | PE/PET | 40/60 | 4.4 | 32 | 20 | 50 | 30 | 256 |
| | Heat-shrinkable fiber | PE/PET | 40/60 | 2.8 | 51 | 30 | 50 | | |
| Example 5 | Heat-shrinkable fiber | PE/PET | 40/60 | 4.4 | 32 | 20 | 70 | 60 | 391 |
| | Heat-shrinkable fiber | PE/PET | 40/60 | 2.8 | 32 | 30 | 30 | | |
| Example 6 | Heat-shrinkable fiber | PE/PET | 40/60 | 4.4 | 32 | 20 | 70 | 90 | 401 |
| | Heat-shrinkable fiber | PE/PET | 40/60 | 2.8 | 32 | 30 | 30 | | |
| Comparative Example 1 | Heat-adhesive fiber | PE/PET | 40/60 | 4.4 | 51 | 1.0 | 100 | 30 | 204 |
| Comparative Example 2 | Heat-adhesive fiber | PE/PET | 40/60 | 4.4 | 51 | 1.0 | 100 | 30 | 206 |

Example 5: Non-woven fabric produced by laminating two sheets of the non-woven fabric of Example 2
Example 6: Non-woven fabric produced by laminating three sheets of the non-woven fabric of Example 2

The index of dispersion for the non-woven fabric of Examples 1 to 6 was within the abovementioned range of 250 to 450. The index of dispersion for the non-woven fabric of Examples 5 (two sheets of the non-woven fabric of Example 2 being laminated) and 6 (three sheets of the non-woven fabric of Example 2 being laminated) showed an approximate value of that of the non-woven fabric of Example 2. Herewith, a similar absorption property to single-layered non-woven fabrics can be expected for multilayered non-woven fabrics.

[Evaluation of Absorption Property]

The absorption property of the non-woven fabric of each Example and Comparative Example as a second sheet arranged between a surface sheet and an absorbent body was measured with artificial urine and artificial menstrual blood.

[Structure of Absorbent Article]

A two-layered non-woven fabric of basis weight 30 g/m² was used for the surface sheet. A top layer thereof was composed of a fiber of sheath-core structure of high-density polyethylene and polyethylene terephthalate, with an average fineness of 3.3 dtex and an average fiber length of 51 millimeters, coated with a hydrophilic oil solution. A bottom layer thereof was composed of a mixed fiber with an equal ratio of: a fiber of sheath-core structure of high-density polyethylene and polyethylene, with an average fineness of 3.3 dtex and an average fiber length of 51 millimeters, coated with a hydrophilic oil solution; and a fiber of sheath-core structure of high-density polyethylene and polyethylene terephthalate, with an average fineness of 2.2 dtex and an average fiber length of 51 millimeters, coated with a hydrophilic oil solution. The ratio of the top layer and the bottom layer was 16:9.

The surface sheet was produced by steps of: forming a top layer fiber web and a bottom layer fiber web by processing the top and the bottom layers of the abovementioned structure by a card machine at the rate of 20 m/min; preparing a fiber web by laminating the top layer fiber web and the bottom layer fiber web; charging the fiber web to a sleeve; conveying the fiber web on an air-permeable net (20 mesh) at a speed of 3 m/min (with the top layer contacting the mesh); and conveying the fiber web with the air-permeable net, in an oven at 125° C. with a hot air volume of 10 Hz, in about 30 seconds. A fluff pulp of 500 g/m² being sandwiched between tissues of 16 g/m² was used for an absorbent body, and adjusted so that the thickness became 5 mm when pinched between tissue of 16 g/m².

A sample absorbent article for measurement of the absorption property was prepared by arranging the non-woven fabrics of Examples and Comparative Examples between the surface sheet and the absorbent body. It should be noted that the non-woven fabrics of Examples 1 to 6 are arranged so that a surface in which the high-density regions are dominantly formed is facing the surface sheet side.

[Evaluation of Absorptive Property by Artificial Urine]

Using the abovementioned sample absorbent article including the non-woven fabrics of Examples 1, 3, 4 and of Comparative Examples 1 and 2, the absorbing speed and surface drying speed thereof for artificial urine was measured according to the following "Evaluation method of absorptive property by artificial urine".

[Evaluation Method of Absorptive Property by Artificial Urine]

(1) Preparation of Artificial Urine

Artificial urine was prepared by adding 200 g of urea (II), 8 g of sodium chloride (salt) (III), 8 g of magnesium sulfate (IV), 3 g of calcium chloride (V), and about 1 g of Brilliant Blue to 10 liters of ion-exchanged water (I).

The absorbing speed and surface drying speed of the artificial urine was measured using: (1) the artificial urine; (2) a burette and a funnel (the burette was adjusted to have a dropping speed of 80 ml/10 sec); (3) a burette stand; (4) a cylinder of 60 mm in diameter and of 550 g; (5) filter paper (e.g., Advantec No. 2, 100 mm*100 mm); (6) a weight of 3.5 kg/100 $cm^2$; (7) a chronograph; (8) an electronic balance; (9) a ruler; (10) a pair of scissors; and the like. The valuation procedure was as follows: (1) Mark a dropping location of the artificial urine using a marker pen; (2) Measure a weight of a sample and a thickness of the dropping location of the artificial urine (confirm a correct weight of the sample); (3) Fix the burette 10 mm above the dropping location; (4) Locate the burette at the dropping location (center of the cylinder) and drip the artificial urine, then start a measurement of absorbing speed; (5) Halt the chronograph once the artificial urine in the cylinder was completely taken in and disappeared from surface (absorption speed); (6) Halt the chronograph once the liquid left on the surface sheet was transferred to the second sheet (surface drying speed). Evaluation according to the abovementioned steps was repeated three times.

Table 2 Shows the Results of Evaluation.

had a high transfer speed from a surface sheet to an absorbent body, but a low absorbing speed.

As described above, absorbent articles including Examples 1, 3, and 4 as a second sheet had a higher absorbing speed and higher transfer speed from a surface sheet to an absorbent body. In other words, the absorbent articles had a property of diffusing a liquid less during transfer and not preventing liquid transfer from the surface sheet to an absorbent body. In other words, non-woven fabrics of Examples 1, 3, and 4 had a property of diffusing a liquid less during transfer and not preventing a liquid transfer from the surface sheet to an absorbent body.

Example 7

A non-woven fabric of Example 7 was produced by folding a non-woven fabric of Example 2 with a side on which high-density regions are dominantly formed facing to the inside.

Example 8

A non-woven fabric of Example 8 was produced by folding a non-woven fabric of Example 2 with a side on which high-density regions are dominantly formed facing to the outside.

The absorption property of non-woven fabric of Examples 7 and 8 and Comparative Examples 1 and 2 as a second sheet was measured with artificial menstrual blood.

[Evaluation of Absorptive Property by Artificial Menstrual Blood]

Using the abovementioned sample absorbent article, an absorbing speed, a surface drying speed, a surface diffusivity, and a rewetting rate (liquid return rate) thereof for artificial menstrual blood was measured according to the following "Evaluation method of absorptive property by artificial menstrual blood".

[Evaluation Method of Absorptive Property by Artificial Menstrual Blood]

(1) Preparation of an Artificial Menstrual Blood

Artificial menstrual blood was prepared by adding the following components to 1 liter of ion-exchanged water.

TABLE 2

| Sample used | | | Example 1 | Example 3 | Example 4 | Comparative Example 1 | Comparative Example 2 |
|---|---|---|---|---|---|---|---|
| Core/Sheath Thickness | (mm) | | 0.67 | 0.68 | 0.66 | 1.4 | 0.30 |
| Density | (g/m³) | | 0.045 | 0.044 | 0.045 | 0.021 | 0.100 |
| Absorbing speed | (s) | 80 ml | 11 | 11 | 11 | 11 | 15 |
| | | 160 ml | 12 | 13 | 12 | 13 | 20 |
| | | 240 ml | 17 | 24 | 18 | 17 | 32 |
| Surface drying speed | (s) | 80 ml | 26 | 30 | 28 | 32 | 28 |
| | | 160 ml | 105 | 154 | 110 | 170 | 130 |
| | | 240 ml | 130 | 218 | 150 | — | 240 |

As shown in Table 2, absorbent articles including Examples 1, 3, and 4 as a second sheet had a high absorbing speed and a high transfer speed from a surface sheet to an absorbent body. On the other hand, Comparative Example 1 had a high absorbing speed, but a low transfer speed from a surface sheet to an absorbent body. Comparative Example 2

| 1 | 80 g of glycerin |
| 2 | 8 g of sodium carboxymethylcellulose (NaCMC) |

-continued

| 3 | 10 g of sodium chloride (NaCl) |
| 4 | 4 g of sodium bicarbonate (NaHCO$_3$) |
| 5 | 8 g of New Coccine |
| 6 | 2 g of Amaranth |
| 7 | 2 g of Sunset Yellow |

An absorbing speed, a surface drying speed, a surface diffusivity, and a rewetting rate of the artificial menstrual blood were measured using: (1) an autoburette (Model 725, manufactured by Metrohm AG); (2) a SKICON; (3) a calorimeter; (4) a perforated acrylic plate (of 200 mm (Length) *100 mm (Width), 130 g, and with a hole of 40 mm*10 mm in the center); (5) scales; (6) a ruler; (7) the artificial menstrual blood; (8) chronographs; (9) filter paper; and the like.

The evaluation procedure was as follows: (1) Place the acrylic plate while adjusting a center of the hole to a center of the sample; (2) Adjust a nozzle of the autoburette 10 mm above the acrylic plate; (3) Drop the artificial menstrual blood for the first time (3 ml at 95 ml/min); (4) Start counting with a chronograph at the beginning of the dropping, and stop counting once the artificial menstrual blood has disappeared from the surface (no motion is detected) to measure an absorbing speed; (5) Start counting with another chronograph at the same time as the stop of the first chronograph, and stop counting once the artificial menstrual blood has disappeared from the surface sheet (no motion is detected) to measure a surface drying speed; (6) Remove the acrylic plate; (7) Measure a spreading area 1 minute after the beginning of the dropping; (8) Drop the artificial menstrual blood for the second time (4 ml at 95 ml/min); (9) Start counting with chronograph at the beginning of the dropping, and stop counting once the artificial menstrual blood has disappeared from the surface (has stopped) to measure an absorbing speed for the second time; (10) Start counting with another chronograph at the same time as the stop of the first chronograph, and stop counting once the artificial menstrual blood has disappeared from the surface sheet (no motion is detected) to measure a surface drying speed for the second time; (11) Remove the acrylic plate; (12) Measure a spreading area 1 minute after the beginning of the dropping; (13) Place filter paper, the acrylic plate, and a weight of 50 g/cm$^2$ on the sample, and leave for 1.5 min; (14) After 1.5 min, weigh the weight of the filter paper to measure a rewetting rate for the first time; (15) Place filter paper, the acrylic plate, and a weight of 100 g/cm$^2$ on the sample, and leave for 1.5 min; (16) After 1.5 min, weigh the weight of the filter paper to measure a rewetting rate for the second time; It should be noted that the spreading area was measured by measuring the length of a major axis and a minor axis that pass through the center of the spreading area of the artificial urine on a second sheet-side surface of the absorbent body. Table 3 shows the results of evaluation.

TABLE 3

| | Surface sheet | | | Second sheet | | | Artificial menstrual blood | | Rewet rate | |
|---|---|---|---|---|---|---|---|---|---|---|
| Sample used | Thickness 3 g/cm$^2$ load | Weight g/m$^2$ | Density g/m$^3$ | Thickness 3 g/cm$^2$ load | Weight g/m$^2$ | Density g/m$^3$ | First dropping 95 ml/min 3 ml after 1 min | Second dropping 95 ml/min + 4 ml after 1 min | 51 g/cm$^2$ after 1.5 min | 106 g/cm$^2$ after 1.5 min |
| Example 7 | 1.71 | 34 | 0.020 | 1.42 | 61 | 0.043 | Absorbing speed: 3.9 s<br>Surface drying speed: 7.0 s<br>Surface diffusivity: 18 * 36 mm | Absorbing speed: 5.2 s<br>Surface drying speed: 9.0 s<br>Surface diffusivity: 19 * 46 mm | 5.7% | 8.5% |
| Example 8 | 1.71 | 34 | 0.020 | 1.45 | 62 | 0.043 | Surface drying speed: 8.0 s<br>Surface diffusivity: 20 * 22 mm | Surface drying speed: 8.0 s<br>Surface diffusivity: 20 * 42 mm | 5.4% | 7.9% |
| Comparative Example 1 | 1.71 | 34 | 0.020 | 2.50 | 147 | 0.059 | Absorbing speed: 5.1 s<br>Surface drying speed: —<br>Surface diffusivity: 44 * 14 mm | Absorbing speed: 7.4 s<br>Surface drying speed: —<br>Surface diffusivity: 47 * 17 mm | 13% | 19% |
| Comparative Example 2 | 1.71 | 34 | 0.020 | 1.50 | 17 | 0.011 | Absorbing speed: 3.8 s<br>Surface drying speed: —<br>Surface diffusivity: 32 * 14 mm | Absorbing speed: 5.8 s<br>Surface drying speed: —<br>Surface diffusivity: 42 * 18 mm | 10% | 15% |

Example 7: Non-woven fabric produced by folding a non-woven fabric of Example 2 with a side on which high-density regions are dominantly formed facing to the inside
Example 8: Non-woven fabric produced by folding a non-woven fabric of Example 2 with a side on which high-density regions are dominantly formed facing to the outside
"Surface drying speed: —" means that the surface is not dry even after 1 min As shown in Table 3, the absorbent articles including non-woven fabric of Examples 7 and 8 as a second sheet have a lower absorbing speed, a lower surface drying speed, and lower surface diffusivity than that of the absorbent articles including non-woven fabric of Comparative Examples 1 and 2 as a second sheet. As a result, absorbent articles using the non-woven fabrics of the examples as a second sheet have a property of diffusing a liquid less during transfer and not preventing liquid transfer from the surface sheet to an absorbent body. In addition, the absorbent articles have a superior surface drying property and a superior repeated drying property. In other words, non-woven fabrics of the present invention have a property of diffusing a liquid less during transfer.

Additionally, as shown in Table 3, the absorbent articles including non-woven fabric of Examples 7 and 8 as a second sheet have a lower rewetting rate than that of the absorbent articles including non-woven fabric of Comparative Examples 1 and 2 as a second sheet. Thus, absorbent articles using the non-woven fabric of the present invention as second sheet have a low rewetting rate. This means that a liquid from a surface sheet can be appropriately transferred to an absorbent body-side.

On the other hand, low-density non-woven fabrics such as Comparative Example 1, have a high absorbing speed, but a lower surface drying speed after that a liquid enters inside a surface sheet. In addition, the low density leads to a low capillary force and liquid cannot be appropriately transferred from a surface sheet. This leads to a lower drying property of a surface sheet. Uniform high-density non-woven fabrics such as Comparative Example 2 have a low absorbing speed and a liquid cannot enter easily inside a surface sheet. The absorbing speed of low-density regions and the liquid drawing ability of high-density regions of the non-woven fabric of the Examples enable transfer of a liquid from a surface sheet to an absorbent body without inhibition.

Next, a non-woven fabric of the second embodiment of the present invention was produced and an absorption property thereof was evaluated in Examples 9 to 11 and Comparative Examples 3 to 5.

Example 9

A non-woven fabric of the Example 9 (of the second embodiment) was produced by the abovementioned third manufacturing method, using a mixed fiber with a 70:30 ratio of: a heat-shrinkable fiber of side-by-side structure of polyethylene-polypropylene copolymer and polypropylene, with an average fineness of 5.6 dtex and an average fiber length of 45 millimeters, coated with a hydrophilic oil solution (melting point: 145° C.); and a heat-adhesive fiber of concentric sheath-core structure of high-density polyethylene and polypropylene, with an average fineness of 3.3 dtex and an average fiber length of 45 millimeters, coated with a hydrophilic oil solution (melting point: 129° C.). It should be noted that the weight of a fiber web before a heat-fusion process was 45 g/m$^2$.

Example 10

A non-woven fabric of Example 10 was produced by a similar method of Example 9 except for a ratio of the heat-shrinkable fiber and the heat-adhesive fiber, which was 50:50. It should be noted that the weight of a fiber web before a heat-fusion process was 45 g/m$^2$.

Example 11

A non-woven fabric of Example 11 was produced by a similar method to Example 9 except for a ratio of the heat-shrinkable fiber and the heat-adhesive fiber, which was 30:70. It should be noted that the weight of a fiber web before a heat-fusion process was 45 g/m$^2$.

Comparative Example 3

A non-woven fabric of Comparative Example 3 was produced by a similar method to Example 9 except that a constitutive fiber is a heat-adhesive fiber of eccentric sheath-core structure of high-density polyethylene and polyethylene, with an average fineness of 4.4 dtex and an average fiber length of 51 millimeters, coated with a hydrophilic oil solution (melting point: 129° C.). It should be noted that the weight of a fiber web before a heat-adhesive process was 145 g/m$^2$.

Comparative Example 4

A non-woven fabric of Comparative Example 4 was produced by a similar method of Comparative Example 3 except that the weight of the fiber web before a heat-fusion process was 22 g/m$^2$.

Comparative Example 5

A non-woven fabric of Comparative Example 5 was produced by a similar method to Example 9 except that a constitutive fiber is a heat-shrinkable fiber of side-by-side structure of polyethylene-polyethylene copolymer and polyethylene, with an average fineness of 5.6 dtex and an average fiber length of 45 millimeters, coated with a hydrophilic oil solution (melting point: 145° C.). It should be noted that the weight of a fiber web before a heat-adhesive process was 15 g/m$^2$.

The weight, thickness, density, and index of dispersion of each non-woven fabric of Examples 9 to 11 and Comparative Examples 3 to 5 are shown in Table 4. Additionally, the temperature conditions of the hot air and the like in the heat-fusion process, and the temperature conditions of the hot air and the like in the heat-shrinkage process of the manufacturing process of each non-woven fabric are shown in Table 4.

TABLE 4

|  | Heat-adhesion process Hot air from above | Heat-shrinkage process Hot air from above and below alternately | Weight after shrinkage (g/m$^2$) | Thickness (3 gf/cm$^2$ load) (mm) | Density (g/m$^3$) | Index of dispersion |
|---|---|---|---|---|---|---|
| Example 9 | 110° C. 10 Hz | 125° C. 60 Hz | 114 | 2.4 | 0.048 | 619 |
| Example 10 | 110° C. 10 Hz | 125° C. 60 Hz | 95 | 1.8 | 0.053 | 549 |
| Example 11 | 110° C. 10 Hz | 125° C. 60 Hz | 58.3 | 1.7 | 0.034 | 390 |
| Comparative example 3 | 110° C. 10 Hz | 130° C. 60 Hz | 147 | 2.5 | 0.059 | 248 |
| Comparative example 4 | 110° C. 10 Hz | 130° C. 60 Hz | 23 | 2.3 | 0.010 | 167 |
| Comparative example 5 | 110° C. 10 Hz | 116° C. 10 Hz | 84.6 | 1.1 | 0.077 | 384 |

The absorption property of non-woven fabric of Examples 9 to 11 and Comparative Examples 3 to 5 as a second sheet arranged between a surface sheet and an absorbent body were measured with artificial menstrual blood.

and a rewetting rate (liquid return rate) thereof for artificial menstrual blood was measured according to the abovementioned "Evaluation method of absorptive property by artificial menstrual blood". Table 5 shows the results of evaluation.

TABLE 5

| | Surface sheet | | | Second sheet | | | | | Rewet rate | |
|---|---|---|---|---|---|---|---|---|---|---|
| | Thickness 3 g/cm$^2$ load | Weight g/m$^2$ | Density g/m$^3$ | Thickness 3 g/cm$^2$ load | Weight g/m$^2$ | Density g/m$^3$ | First dropping 95 ml/min 3 ml after 1 min | Second dropping 95 ml/min + 4 ml after 1 min | 51 g/cm$^2$ after 1.5 min | 106 g/cm$^2$ after 1.5 min |
| Example 9 | 1.71 | 34 | 0.020 | 2.44 | 114 | 0.047 | Absorbing speed: 3.3 s<br>Surface drying speed: 5 s<br>Surface diffusivity: 14 * 38 mm | Absorbing speed: 5.6 s<br>Surface drying speed: 10 s<br>Surface diffusivity: 16 * 43 mm | 0.2% | 0.4% |
| Example 10 | 1.71 | 34 | 0.020 | 1.80 | 95 | 0.053 | Absorbing speed: 3.8 s<br>Surface drying speed: 9 s<br>Surface diffusivity: 12 * 36 mm | Absorbing speed: 6.8 s<br>Surface drying speed: 11 s<br>Surface diffusivity: 14 * 44 mm | 0.2% | 0.4% |
| Example 11 | 1.71 | 34 | 0.020 | 1.70 | 58 | 0.034 | Absorbing speed: 4.7 s<br>Surface drying speed: 6 s<br>Surface diffusivity: 14 * 41 mm | Absorbing speed: 6.2 s<br>Surface drying speed: 14 s<br>Surface diffusivity: 16 * 44 mm | 0.9% | 1.0% |
| Comparative Example 3 | 1.71 | 34 | 0.020 | 2.50 | 147 | 0.059 | Absorbing speed: 5.1 s<br>Complete drying speed: —<br>Surface diffusivity: 44 * 14 mm | Absorbing speed: 7.4 s<br>Complete drying speed: —<br>Surface diffusivity: 47 * 17 mm | 13% | 19% |
| Comparative Example 4 | 1.71 | 34 | 0.020 | 1.50 | 17 | 0.011 | Absorbing speed: 3.8 s<br>Surface drying speed: —<br>Surface diffusivity: 32 * 14 mm | Absorbing speed: 5.8 s<br>Surface drying speed: —<br>Surface diffusivity: 42 * 18 mm | 10% | 15% |
| Comparative Example 5 | 1.71 | 34 | 0.020 | 1.10 | 85 | 0.077 | Absorbing speed: 4.3 s<br>Surface drying speed: 17 s<br>Surface diffusivity: 11 * 40 mm | Absorbing speed: 7.4 s<br>Surface drying speed: 8 s<br>Surface diffusivity: 16 * 48 mm | 2.7% | 4.8% |

"Complete drying speed: —" means that the surface is not dry even after 1 min

[Structure of Absorbent Article]

A non-woven fabric of weight 40 g/m$^2$ was used for the surface sheet. A mixed fiber with a 70:30 ratio of: a fiber of sheath-core structure of high-density polyethylene and polyethylene, with an average fineness of 3.3 dtex and an average fiber length of 51 millimeters, coated with a hydrophilic oil solution; and a fiber coated with a water-repellent oil solution was used as a constitutive fiber of the non-woven fabric.

The surface sheet was produced by steps of: forming a fiber web by processing a fiber aggregate of the abovementioned structure by a card machine at the rate of 20 m/min; preparing a fiber web by laminating the top layer fiber web and the bottom layer fiber web; charging the fiber web to a sleeve; conveying the fiber web on an air-permeable net (20 mesh) at a speed of 3 m/min (with the top layer contacting the mesh); and conveying the fiber web with the air-permeable net, in an oven at 125° C. with a hot air volume of 10 Hz, in about 30 seconds. A fluff pulp of 500 g/m$^2$ being sandwiched between tissues of 16 g/m$^2$ was used for an absorbent body.

A sample absorbent article for measurement of the absorption property was prepared by arranging the non-woven fabrics of Examples and Comparative Examples between the surface sheet and the absorbent body.

[Evaluation of the Absorptive Property by Artificial Menstrual Blood]

Using the abovementioned sample absorbent article, an absorbing speed, a surface drying speed, surface diffusivity, As shown in Table 5, the absorbent articles including non-woven fabric of Examples 9 to 11 as a second sheet have a lower absorbing speed, a lower surface drying speed, and a lower surface diffusivity than that of the absorbent articles including non-woven fabric of Comparative Examples 1 to 3 as a second sheet. As a result, absorbent articles using non-woven fabrics of the Examples as a second sheet had a property of diffusing a liquid less during transfer and not preventing a liquid transfer from the surface sheet to an absorbent body. In addition, the absorbent articles have a superior surface drying property and a superior repeated drying property. In other words, the non-woven fabric of the present invention has a property of diffusing a liquid less during transfer and not preventing liquid transfer from the surface sheet to an absorbent body.

Additionally, the absorbent articles including non-woven fabric of Examples 9 to 11 as a second sheet have a lower rewetting rate than that of the absorbent articles including non-woven fabric of Examples 1 to 3 as a second sheet. Thus, absorbent articles using the non-woven fabric of the present invention as a second sheet have a low rewetting rate. This means that a liquid from a surface sheet can be appropriately transferred to an absorbent body-side.

What is claimed is:

1. A method of manufacturing a nonwoven fabric of substantially uniform thickness, the nonwoven fabric having heat-adhesive heat-shrinkable fibers, the method comprising:

a heat shrinkage process in which a fiber web having the heat-adhesive heat-shrinkable fibers is heat processed at a temperature at which the heat-shrinkable fibers can be melted and shrunk, and a pressing process in which a plurality of convex portions, generated on at least one side of the fiber web by a heat process in the heat shrinkage process which heat-shrinks the heat-shrinkable fibers, are pressed in a thickness direction of the fiber web, whereby the nonwoven fabric is provided with a plurality of high density regions formed dominantly on at least one side in a thickness direction of the nonwoven fabric and having a higher density than an average density of the nonwoven fabric, and the nonwoven fabric is provided with a plurality of low density regions having a lower density than the average density, wherein the plurality of high density regions and the plurality of low density regions are dispersedly formed in a planar direction perpendicular to the thickness direction of the nonwoven fabric and at least a portion of the plurality of low density regions extend across both sides of the nonwoven fabric in the thickness direction.

2. The non-woven fabric manufacturing method according to claim 1, wherein:

in the heat shrinkage process thereof, the fiber web is heat-processed while being vertically supported from below by way of a lower supporting member having a substantially planate surface, with the heat-shrinkable fiber being restrained from heat-shrinking in a surface supported by the lower supporting member; and in the pressing process, the heat-processed fiber web is pressed from an opposite side of the side supported by the lower supporting member.

3. A method of manufacturing a nonwoven fabric of substantially uniform thickness, the nonwoven fabric having heat-adhesive fibers and heat-shrinkable fibers having crimpability at least when heat-shrunk, the method comprising:

a feeding process in which a fiber web having the heat-adhesive fibers and the heat shrinkable fibers is conveyed to a predetermined heating device, a heat shrinkage process in which the fiber web is conveyed in a predetermined direction and heat-processed at a temperature at which the heat-shrinkable fibers can be shrunk, whereby the nonwoven fabric is provided with a plurality of high density regions formed mainly of the heat-shrinkable fibers being heat-shrunk and having a higher density than an average density of the nonwoven fabric, and the nonwoven fabric is provided with a plurality of low density regions formed mainly of the heat-adhesive fibers being adhered to each other and having a lower density than the average density, wherein the plurality of high density regions and the plurality of low density regions are dispersedly formed in a planar direction perpendicular to a thickness direction of the nonwoven fabric and at least a portion of the plurality of low density regions extend across both sides of the nonwoven fabric in the thickness direction, and wherein a condition of the high density and low density regions is regulated by adjusting the feeding speed of the fiber web in at least one of the feeding process and the heat shrinkage process.

4. The non-woven fabric manufacturing method according to claim 1, wherein the feeding speed of the fiber web in the heat shrinkage process is adjusted so that a ratio of the feeding speed of the fiber web in the heat shrinkage process to the feeding speed of the fiber web in the feeding process is larger than a heat-shrinkage ratio of the fiber web at the temperature in the heat shrinkage process.

5. The non-woven fabric manufacturing method according to claim 1, comprising a pre-heating process prior to the heat-shrinkage process in which the fiber web is heated at a temperature at which the heat-adhesive fiber is not substantially melted and the heat-shrinkable fiber is not substantially shrunk, to limit a degree of freedom of the heat-shrinkable fiber by reducing a thickness of the fiber web.

6. The non-woven fabric manufacturing method according to claim 3, comprising a heat-fusion process prior to the heat-shrinkage process, wherein the fiber web is heated at a temperature at which the heat-adhesive fiber may be melted and the heat-shrinkable fiber is not substantially shrunk.

7. The non-woven fabric manufacturing method according to claim 3, wherein, in the heat shrinkage process, the fiber web is conveyed while being disposed between an air permeable first supporting member and an air permeable second supporting member, which is arranged vertically above and substantially parallel to the first supporting member with a predetermined distance away therefrom, and heat-processed while being at least partially spaced apart from at least one of the first supporting member and the second supporting member by emitting heated air of a predetermined temperature from vertically under the first supporting member and emitting heated air of a predetermined temperature from vertically above the second supporting member.

* * * * *